US010646512B2

(12) United States Patent
Halphen et al.

(10) Patent No.: US 10,646,512 B2
(45) Date of Patent: *May 12, 2020

(54) COLONOSCOPY - PREPARATION

(71) Applicant: NORGINE BV, Amsterdam Zuid-Oost OT (NL)

(72) Inventors: Marc Halphen, London (GB); Hans-Jurgen Gruss, London (GB); Ian Cox, London (GB); Alasdair Cockett, London (GB); Peter Stein, Amsterdam (NL); Alex Ungar, Wigton (GB)

(73) Assignee: NORGINE BV, Amsterdam (NL)

( * ) Notice: Subject to any disclaimer, the term of this patent is extended or adjusted under 35 U.S.C. 154(b) by 16 days.

This patent is subject to a terminal disclaimer.

(21) Appl. No.: 15/407,080

(22) Filed: Jan. 16, 2017

(65) Prior Publication Data

US 2017/0119816 A1 May 4, 2017

Related U.S. Application Data

(63) Continuation of application No. 14/004,604, filed as application No. PCT/GB2012/050526 on Mar. 9, 2012, now Pat. No. 9,592,252.

(30) Foreign Application Priority Data

| Mar. 11, 2011 | (GB) | ................................ 1104200.9 |
| Mar. 11, 2011 | (GB) | ................................ 1104202.5 |
| Aug. 23, 2011 | (GB) | ................................ 1114629.7 |

(51) Int. Cl.
| A61K 31/375 | (2006.01) |
| A61K 31/765 | (2006.01) |
| A61K 47/06 | (2006.01) |
| A61K 47/22 | (2006.01) |
| A61K 9/08 | (2006.01) |
| A61K 33/04 | (2006.01) |
| A61K 33/14 | (2006.01) |
| A61K 9/00 | (2006.01) |
| A61K 47/02 | (2006.01) |
| A61K 31/77 | (2006.01) |

(52) U.S. Cl.
CPC ............ *A61K 33/14* (2013.01); *A61K 9/0095* (2013.01); *A61K 9/08* (2013.01); *A61K 31/375* (2013.01); *A61K 31/765* (2013.01); *A61K 31/77* (2013.01); *A61K 33/04* (2013.01); *A61K 47/02* (2013.01); *A61K 47/22* (2013.01)

(58) Field of Classification Search
CPC ...... A61K 47/22; A61K 31/375; A61K 31/77; A61K 31/765
See application file for complete search history.

(56) References Cited

U.S. PATENT DOCUMENTS

| 2,187,467 A | 1/1940 | Stuart |
| 2,427,692 A | 9/1947 | Ruskin |
| 2,481,353 A | 9/1949 | Schnabel |
| 2,694,719 A | 11/1954 | Opplt |
| 3,211,614 A | 10/1965 | Embring et al. |
| 5,274,001 A * | 12/1993 | Borody ................ A61K 31/375 514/474 |
| 5,281,606 A | 1/1994 | Guzzi et al. |
| 5,411,745 A | 5/1995 | Oshlack et al. |
| 5,540,945 A | 7/1996 | Ikushima et al. |
| 5,858,403 A | 1/1999 | Borody et al. |
| 6,121,250 A | 9/2000 | Nishiyama et al. |
| 6,162,464 A | 12/2000 | Jacob et al. |
| 6,444,198 B1 | 9/2002 | Daggy et al. |
| 6,592,901 B2 | 7/2003 | Durig et al. |
| 6,946,149 B2 | 9/2005 | Cleveland |
| 2004/0143005 A1 * | 7/2004 | Barras .................... A61K 9/009 514/474 |
| 2004/0171691 A1 | 9/2004 | Tang et al. |
| 2005/0079216 A1 | 4/2005 | Petereit et al. |
| 2005/0129781 A1 | 6/2005 | Skiendzielewski et al. |
| 2005/0152989 A1 | 7/2005 | Pelham et al. |
| 2005/0226906 A1 | 10/2005 | Moneymaker et al. |
| 2006/0029570 A1 | 2/2006 | Aronson et al. |

(Continued)

FOREIGN PATENT DOCUMENTS

| AU | 2011101324 A4 | 11/2011 |
| CN | 1150021 A | 5/1997 |

(Continued)

OTHER PUBLICATIONS

Hornig, "Absorption of large, single, oral intakes of ascorbic acid", Int. J Vit Nutr Res 50: 309 (1980) (Year: 1980).*
Owaki and Baba, "Method for the Pretreatment with Magcorol P Solutions", Therapeutic Res 14 (S2): 189-191 (1993) (Year: 1993).*
3okemeyer, B. "Koloskopievorbereitung in der ambulanten Gastroenterologie", Verdauungskrankheiten, 18: 17-24 (2000).
Cohen, Lawrence B, "Split dosing of bowel preparations for colonoscopy: an analysis of its efficacy, safety, and tolerability", Gastrointestinal Endoscopy, 72(2): 406-412 (2010).
Rex et al., "A randomized, controlled trial of oral sulfate solution plus polyethylene glycol as a bowel preparation for colonoscopy", Gastrointestinal Endoscopy, 80(3): 482-491 (2014).

(Continued)

*Primary Examiner* — Alton N Pryor
(74) *Attorney, Agent, or Firm* — Yankwich & Associates, P.C.; Leon R. Yankwich; Michael R. Wesolowski

(57) ABSTRACT

The invention provides a colon cleansing solution comprising: a) 300 to 2000 mmol per litre ascorbate anion provided by ascorbic acid, one or more salts of ascorbic acid, or a mixture thereof; and b) 10 to 200 g per litre polyethylene glycol. The invention also provides methods and kits associated with, or making use of the solutions. The invention also provides a method of cleansing the colon of a subject comprising: —administering to the subject an effect amount of a first cleansing solution; and then after a time interval— administering to the subject an effective amount of a second cleansing solution, wherein the two cleansing solutions are as described in the specification.

16 Claims, 2 Drawing Sheets

(56) References Cited

U.S. PATENT DOCUMENTS

| | | |
|---|---|---|
| 2007/0298100 A1 | 12/2007 | Barras et al. |
| 2008/0193523 A1 | 8/2008 | Heim et al. |
| 2008/0260682 A1 | 10/2008 | Rose et al. |
| 2009/0062387 A1 | 3/2009 | Caswell et al. |
| 2009/0258090 A1 | 10/2009 | Cleveland |
| 2009/0232943 A1 | 12/2009 | Johnson et al. |
| 2009/0324736 A1 | 12/2009 | Johnson et al. |
| 2010/0178360 A1 | 7/2010 | Deviere et al. |
| 2010/0255122 A1 | 10/2010 | Garren et al. |
| 2010/0297264 A1* | 11/2010 | Kastenberg .......... A61K 9/0095 424/680 |
| 2011/0189091 A1* | 8/2011 | Bachwich ................ A61K 9/08 424/9.1 |
| 2011/0289091 A1* | 11/2011 | Collins ............. G06F 17/30321 707/741 |
| 2012/0135090 A1 | 5/2012 | Seldon et al. |
| 2012/0195980 A1 | 8/2012 | Shaver |
| 2013/0102661 A1 | 4/2013 | Chan |
| 2013/0121916 A1 | 5/2013 | Baroni et al. |
| 2013/0136806 A1 | 5/2013 | Zanarotti et al. |
| 2013/0149390 A1 | 6/2013 | Gorelick et al. |
| 2013/0156871 A1 | 6/2013 | Keller |
| 2013/0304016 A1 | 11/2013 | Kouno et al. |

FOREIGN PATENT DOCUMENTS

| | | | |
|---|---|---|---|
| CN | 1093259 | | 4/1998 |
| CN | 1371688 | | 10/2002 |
| CN | 1813674 | | 8/2006 |
| CN | 101450074 | | 6/2009 |
| CN | 101496589 | | 8/2009 |
| CN | 101766563 | | 7/2010 |
| CN | 102805752 | A | 5/2012 |
| CN | 102600201 | | 7/2012 |
| CN | 102772427 | A | 11/2012 |
| CN | 102805753 | A | 12/2012 |
| CN | 103550212 | | 2/2014 |
| CN | 103550249 | A | 2/2014 |
| DE | 3807712 | A | 2/1989 |
| DE | 10239161 | | 3/2004 |
| DE | 202010016398 | U1 | 12/2010 |
| EP | 0436061 | | 7/1991 |
| EP | 0441786 | | 10/1995 |
| EP | 2322190 | A1 | 5/2011 |
| GB | 2471954 | | 1/2011 |
| IN | 00090MA1995 | | 2/2005 |
| IN | 1995MA00189 | | 2/2005 |
| IN | 00458CH2005 | | 1/2011 |
| JP | 6295194 | | 5/1987 |
| JP | 1-125319 | A | 5/1989 |
| JP | 1-132527 | | 5/1989 |
| JP | 2630423 | | 11/1989 |
| JP | 3-168067 | | 7/1991 |
| JP | 4-112830 | A | 4/1992 |
| JP | H04112830 | A | 4/1992 |
| JP | 2557111 | | 9/1996 |
| JP | 11-228423 | A | 8/1999 |
| JP | 2002-265372 | A | 9/2002 |
| JP | 2003-73260 | A | 3/2003 |
| JP | 3439559 | B2 | 6/2003 |
| JP | 3457012 | | 8/2003 |
| JP | 2004-323456 | | 11/2004 |
| JP | 2004-323479 | | 11/2004 |
| JP | 3850891 | | 9/2006 |
| JP | 2012-207002 | | 10/2012 |
| RU | 2178292 | C1 | 4/2001 |
| WO | WO1987/00754 | | 2/1987 |
| WO | WO1989/05659 | | 6/1989 |
| WO | WO2000/49414 | | 8/2000 |
| WO | WO2002/00043 | | 1/2002 |
| WO | WO2003/037298 | | 5/2003 |
| WO | WO2004/037292 | | 5/2004 |
| WO | WO2005/049049 | | 6/2005 |
| WO | WO2005/120501 | | 12/2005 |
| WO | WO2007/037803 | | 4/2007 |
| WO | WO2007/044681 | | 4/2007 |
| WO | WO2009/052256 | | 4/2009 |
| WO | WO-2009052256 | A2 * | 4/2009 .......... A61K 9/0095 |
| WO | WO2009056114 | A2 | 5/2009 |
| WO | WO2010/123901 | | 10/2010 |
| WO | WO2011/007153 | | 1/2011 |
| WO | WO2011/107007 | A1 | 9/2011 |
| WO | WO2012/059725 | A1 | 5/2012 |
| WO | WO2012059724 | A1 | 5/2012 |
| WO | WO2012/104617 | A1 | 8/2012 |
| WO | WO2012/120027 | | 9/2012 |
| WO | WO2012/123720 | | 9/2012 |
| WO | WO2013/039477 | | 3/2013 |
| WO | WO2013/059881 | | 5/2013 |
| WO | WO2013/119002 | | 8/2013 |

OTHER PUBLICATIONS

Marmo, Riccardo et al., "Effective bowel cleansing before colonoscopy: a randomized study of split-dosage versus non-split dosage regimens of high-volume versus low-volume polyethylene glycol solutions", Gastrointestinal Endoscopy, vol. 72, Issue 2: 313-320 (2010).

Adams et al., "Bisacodyl Reduces the Volume of Polyethylene Glycol Solution Required for Bowel Preparation", Dis. Colon Recutm, 37(3): 229-233 (1994).

Agus et al., "Stromal Cell Oxidation: A Mechanism by Which Tumors Obtain Vitamin C", Cancer Research, 59: 4555-4558 (1999).

Agus et al., Vitamin C Crosses the Blood-Brain Barrier in the Oxidized Form Through the Glucose Transporters, J. Clin. Invest., 100(11): 2842-2848 (1997).

Arora et al., "Use of Powder PEG-3350 as a Sole Bowel Preparation: Clinical Case Series of 245 Patients", Gastroenterology & Hepatology, 4(7): 489-492 (2008).

Auer et al., "Relative hyperoxaluria, crystalluria and haematuria after megadose ingestion of vitamin C", Eur. J. Clin. Invest., 28: 695-700 (1998).

Auer et al., "The Effect of Ascorbic Acid Ingestion on the Biochemical and Physico-chemical Risk Factors Associated with Calcium Oxalate Kidney Stone Formation", Clin. Chem. Lab. Med., 36(3): 143-148 (1998).

Barkun et al., "Commonly used preparations for colonoscopy: Efficacy, tolerability and safety—A Canadian Association of Gastroenterology position paper", Can. J. Gastroenterol., 20(11): 699-710 (2006).

Blanchard et al., "Pharmacokinetic perspectives on megadose of ascorbic acid", Am. J. Clin. Nutr., 66: 1165-1171 (1997).

Bokemeyer, B. "Koloskopievorbereitung in der ambulanten Gastroenterologie", Verdauungskranheiten, 18: 17-24 (2000).

Calabria et al., "Effect of vitamin C supplements on urinary oxalate and pH in calcium stone-forming patients", Kidney International, 63: 1066-1071 (2003).

Cho et al., "A Prospective Randomized Trial Comparing Divided Dose of Polyethylene Glycol (PEG) Solution With Stimulant Laxative Plus Low Dose PEG Solution for Colon Cleansing", Endoscopy, 37(Suppl. I) A275 (2005).

Doward et al., "Development and validation of the Bowel Cleansing Impact Review (BOCLIR)", Frontline Gastroenterology, 4: 112-119 (2013).

Duconge et al., "Pharmacokinetics of Vitamin C: insights into the oral and intravenous administration of ascorbate", PRHSJ, 27(1): 7-19 (2008).

Graumlich et al., "Pharmacokinetic Model of Ascorbic Acid in Healthy Male Volunteers During Depletion and Repletion", Pharmaceutical Research, 14(9): 1133-1139 (1997).

Gruss et al., "Pharmacokinetic Modelling of a Healthy Volunteer Study for the Assessments of the Ascorbic Acid Effects in PEG+E Containing Gut Cleansing Solutions", Gastrointest. Endosc., 67(5): AB324-AB325 (2008).

Halphen et al., "Validation of the Harefield Cleansing Scale: a tool for the evaluation of bowel cleansing quality in both research and clinical practice", Gastrointestinal Endoscopy, 78(1): 121-131 (2013).

Hathcock et al., "Vitamins E and C are safe across a broad range of intakes", Am. J. Clin. Nutr., 81: 736-745 (2005).

(56) References Cited

OTHER PUBLICATIONS

Hawes et al., A consensus document on bowel preparation before colonoscopy: Prepared by a Task Force From the American Society of Colon and Rectal Surgeons (ASCRS), the American Society for Gastrointestinal Endoscopy (ASGE), and the Society of American Gastrointestinal and Endoscopic surgeons (SAGES),63(7): 894-909 (2006).
Hickey et al., "Pharmacokinetics of oral vitamin C", Journal of Nutritional & Environmental Medicine, 17(3): 169-177 (2008).
Hornig et al., "Absorption of Large, Single, Oral Intakes of Ascorbic Acid", Internat. J. Vit. Nutr. Res., 50: 309-314 (1980).
Jackson et al., "Screening for Vitamin C in the Urine: Is it Clinically Significant?", Journal of Orthomolecular Medicine, 20(4): 259-261 (2005).
Jacob et al., Biochemical indices of human vitamin C status 1-3, Am. J. Clin. Nutr., 46: 818-826 (1987).
Kallner et al., "Steady-state turnover and body pool of ascorbic acid in man", Am. J. Clin. Nutr., 32: 530-539 (1979).
Lamarche et al., "Vitamin C-Induced Oxalate Nephropathy", International Journal of Nephrology, 1-4 (2011).
Levine et al., "Vitamin C pharmacokinetics in healthy volunteers: Evidence for a recommended dietary allowance", Proc. Natl. Acad. Sci. USA, 93: 3704-3709 (1996).
Levine et al., "Vitamin C: A Concentration-Function Approach Yields Pharmacology and Therapeutic Discoveries", American Society for Nutrition Adv. Nutr., 78-88 (2011).
Lykkesfeldt, "Cancer Epidemiology Biomarkers & Prevention", Cancer Epidemiology, Biomarkers and Prevention, 16: 2513-2516 (2007).
Malo et al., "Glucose Modulates Vitamin C Transport in Adult Human Small Intestinal Brush Border Membrane Vesicles", American Society for Nutritional Sciences, 63-69 (1999).
Mamula et al., "Colonoscopy preparation", Gastrointestinal Endoscopy, 69(7): 1201-1209 (2009).
Massey et al., "Ascorbate Increases Human Oxaluria and Kidney Stone Risk", American Society for Nutritional Sciences 1673-1677 (2005).
May, J., "The SLC23 family of ascorbate transporters: ensuring that you get and keep your daily dose of vitamin C", British Journal of Pharmacology, 164: 1793-1801 (2011).
May et al., "Nitric Oxide Mediates Tightening of the Endothelial Barrier by Ascorbic Acid", Biochem. Biophys. Res. Commun., 404(2); 701-705 (2011).
Mouly et al., "Effects of the Addition of High-Dose Vitamin C to Polyethylene Glycol Solution for Colonic Cleansing: A Pilot Study in Healthy Volunteers", Current Therapeutic Research, 66(6): 286-500 (2005).
MOVIPREP, Summary of Product Characteristics as revised Jan. 18, 2011.
Ohno et al., "High-dose Vitamin C (Ascorbic Acid) Therapy in the Treatment of Patients with Advanced Cancer", Anticancer Search, 29: 809-816 (2009).
Owaki et al., "Method for Pretreatment with Magcorol P Solutions", Therapeutic Research, 14: (Suppl. 2): 189-191 (1993).
Padayatty et al., "Vitamin C Pharmacokinetics: Implications for Oral and Intravenous Use", Annals of Internal Medicine, 140(7): 533-538 (2004).
Parente et al., "Bowel preparation before colonoscopy in the era of mass screening for colo-rectal cancer: A practical approach", Digestive and Liver Disease, 41: 87-95 (2009).
Park et al., "Efficacy and Tolerability of Split-Dose Magnesium Citrate: Low-Volume (2 Liters) Polyethylene Glycol vs. Single- or Split-Dose Polyethlene Glycol Bowel Preparation for Morning Colonoscopy", Am. J. Gastroenterol., 105: 1319-1326 (2010).
Piotrovskij et al., "The Use of a Nonlinear Absorption Model in the Study of Ascorbic Acid Bioavailability in Man", Biopharmaceutics and Drug Disposition, 14: 429-442 (1993).
Puxty et al., "Golytely: A New Approach to Faecal Impaction in Old Age", Age and Ageing, 15: 182-184 (1986).
Ralli et al., "The Mechanism of the Excretion of Vitamin C by the Human Kidney", Journal of Clinical Investigation, 19 (5): 765-770 (1940).
Riordan et al., Clinical and Experimental Experiences with Intravenous Vitamin C, Journal of Orthomolecular Medicine, 15(4): 201-213 (2000).
Schanz et al., "Bowel Preparation for Colonoscopy with Sodium Phosphate Solution versus Polyethylene Glycol-Based Lavage: A Multicenter Trial", Diagnostic and Therapeutic Endoscopy, 2008: 1-6 (2008).
Vitamin and Mineral Requirements in Human Nutrition, Second Edition, 2004 Report of a Joint FAO/WHO Expert Consultation, Bangkok, Thailand, Sep. 21-30, 1998.
Wexner et al., "ASGE/ASCRS/SAGES Guidelines for Bowel Preparation Prior to Colonoscopy" (2006).
Wexner et al., "Guideline Summary NGC-5139", A Consensus Document on Bowel Preparation Before Colonoscopy, (2011).
Smith, Lendon H. "Clinical Guide to the Use of Vitamin C", 2004.
Hawes et al., Gastrointestinal Endoscopy, 63(7): 894-909 (2006).
Bisschops et al., "Colon cleansing efficacy and safety with 1 L NER1006 versus 2 L polyethylene glycol + ascorbate: a randomized phase 3 trial", Endoscopy, 51(01): 60-72 (2019).
Bitoun, A. et al., Results of a prospective randomised multicentre controlled trial comparing a new 2-L ascorbic acid plus polyethylene glycol and electrolyte solution vs. sodium phosphate solution in patients undergoing elective colonoscopy, Aliment Pharmacol Ther 24, 1631-1642 (2006).
Chiu, Han-Mo, M.D., et al., The Impact of Colon Preparation Timing on Colonoscopic Detection of Colorectal Neoplasms—A Prospective Endoscopist-Blinded Randomized Trial, Am J Gastroenterol 101: 2719-2725 (2006).
Church, James M., M.D., Effectiveness of Polyethylene Glycol Antegrade Gut Lavage Bowel preparation for Colonoscopy—Timing is the Key!, Dis Colon Rectum 41: 1223-1225 (1998).

\* cited by examiner

COLONOSCOPY - PREPARATION

CROSS-REFERENCE TO RELATED APPLICATIONS

This application is continuation of pending U.S. application Ser. No. 14/004,604, filed Sep. 11, 2013, which application is a United States national stage filing under 35 U.S.C. § 371 of international (PCT) application no. PCT/GB2012/050526, filed Mar. 9, 2012, and designating the United States, which claims priority to United Kingdom (GB) Appln. Nos. 1104202.5, filed Mar. 11, 2011; 1104200.9, filed Mar. 11, 2011; and 1114629.7, filed Aug. 23, 2011.

The present invention relates to a method of cleansing the colon using colon cleansing solutions, and compositions and kits associated therewith. Colon cleansing compositions are also known as lavage solutions, bowel cleansers, purgatives or colonic evacuants.

Colon or bowel cleansing is important before numerous surgical or diagnostic procedures, including colonoscopy, barium enema examination, sigmoidoscopy and colon surgery. Such procedures are often carried out on an outpatient basis and thus it is desirable that the colon cleansing be carried out by the patient at home, prior to arrival at the hospital or surgery where the procedure is to take place. It is therefore important that patient compliance is good without medical supervision if satisfactory colon cleansing is to be achieved prior to the procedure.

Intestinal lavage, in which a large volume of an electrolyte solution containing sodium sulphate and polyethylene glycol is ingested, is one of the most common methods for colon cleansing. These osmotically active agents are non-absorbable or only poorly absorbable and thus retain water in the bowel, resulting in copious diarrhoea and cleansing of the colon.

For effective cleansing, many of these compositions must be ingested in quantities of between 2 to 4 litres. The unpleasant taste of these compositions combined with the large volumes required to be ingested often contributes to nausea or vomiting, resulting in poor patient compliance and failure to consume the full volume of solution. Poor patient compliance can lead to inadequate preparation of the colon which can, in turn, lead to cancellation or repetition of the colonoscopy becoming necessary or, worse, non-detection of lesions or polyps indicative of cancer risk.

A number of improved colon cleansing compositions are described in WO 2004/037292. A colon cleansing composition according to WO 2004/037292 that comprises polyethylene glycol 3350, sodium sulphate, an ascorbate component, electrolytes, sweetener and flavouring is commercialised as a powder for oral solution under the tradename MOVIPREP® (registered trademark of Velinor AG, a member of the Norgine group of companies). The MOVIPREP solution is effective despite being taken in a substantially lower volume than other colon cleansing solutions. Typically, only 2 litres of the solution need to be taken by an adult patient, a significant benefit when compared to taking 4 litres of previous solutions.

Various regimens for the timing of ingestion of colon cleansing solutions are mentioned in the literature and in patient information leaflets that accompany colon cleansing products. For example, the MOVIPREP solution mentioned above may be taken (optionally with additional clear liquids also optionally being taken) in the evening before the examination or procedure, or the MOVIPREP solution may be taken in a "split-dose" regimen, with approximately half of the cleansing solution being taken the evening before the examination or procedure ("first dose"), and the remainder being taken the following morning ("second dose").

Despite the advances that have been made, all colon cleansing products on the market continue to require a subject to ingest a large volume of solution (2 litres in the case of the MOVIPREP solution). Many subjects find the ingestion of a large volume unpleasant or difficult and poor patient compliance thus remains a problem. There remains a need for alternative colon cleansing solutions that are effective when ingested in small volumes.

When comparing the pharmacokinetic profiles of the components of the MOVIPREP solution (ascorbate component, sodium sulphate, PEG 3350 and electrolytes) in subjects who had taken the solution in the "evening before" regimen with the pharmacokinetic profiles in subjects who had taken the solution in the "split-dose" regimen in a clinical study, the present inventors found that a surprisingly high proportion of the ascorbate component of the first dose of the "split-dose" regimen was absorbed into the subjects' circulations. The proportion of the ascorbate component that was found to be absorbed into the circulation was then excreted in the subjects' urine over time, rather than being expelled in faeces. Whilst this absorption into the circulation is not harmful to the subject, it does reduce the osmotic strength of the solution, and hence it reduces the solution's ability to cleanse the colon. It is also wasteful of the component. The finding was surprising in view of the commonly accepted view in the literature that a maximum of 3 g of ascorbic acid can be absorbed in the intestines per day (Hornig, D. et al., Int. J. Vit. Nutr. Res., 1980, 50, 309). Ascorbate-containing colon cleansing solutions have to date been formulated on that basis.

The invention thus provides, in a first aspect, a colon cleansing solution comprising:
a) 300 to 2000 mmol per litre ascorbate anion provided by ascorbic acid, one or more salts of ascorbic acid, or a mixture thereof; and
b) 10 to 200 g per litre polyethylene glycol.

The solution of the invention is a surprisingly effective colon cleansing solution as measured by stool output, providing satisfactory clearance of stools from the colon with ingestion of a smaller total volume of solution than with the standard 2 or 4 litre solutions of the prior art.

The ascorbate anion may be provided by ascorbic acid, by one or more salts of ascorbic acid, or by a mixture of ascorbic acid and one or more salts of ascorbic acid. For convenience, they will be referred to herein as the "ascorbate component". Suitable salts include alkali metal salts and alkaline earth metal salts. For example a salt may be selected from sodium, potassium, magnesium and calcium salts. For example, preferred salts of ascorbic acid include sodium ascorbate, potassium ascorbate, magnesium ascorbate and calcium ascorbate. In an embodiment, the ascorbate anion is provided by ascorbic acid, one or more salts of ascorbic acid selected from sodium ascorbate, potassium ascorbate, magnesium ascorbate and calcium ascorbate, or a mixture thereof. Particularly preferred salts of ascorbic acid are magnesium ascorbate and sodium ascorbate, for example sodium ascorbate. In one embodiment, the solution comprises ascorbic acid and one or more salts of ascorbic acid (and preferably no further ascorbate), for example ascorbic acid and sodium ascorbate (and preferably no further ascorbate), or ascorbic acid and magnesium ascorbate (and preferably no further ascorbate).

The solution of the invention preferably comprises ascorbate anion in a concentration of: 300-1500 mmol per litre, for example 300-1200 mmol per litre, for example 300-1000 mmol per litre, for example 300-850 mmol per litre, for example 350-800 mmol per litre, for example 400-700 mmol per litre.

Ascorbic acid has a molecular weight of 176 g/mol. Accordingly, the 300 to 2000 mmol ascorbate anion per litre can be provided by 52.8 to 352 g/litre ascorbic acid.

Sodium ascorbate has a molecular weight of 198 g/mol. Accordingly, the 300 to 2000 mmol ascorbate anion per litre can be provided by 59.4 to 396 g/litre sodium ascorbate.

Potassium ascorbate has a molecular weight of 214 g/mol. Accordingly, the 300 to 2000 mmol ascorbate anion per litre can be provided by 64.2 to 428 g/litre potassium ascorbate.

Magnesium ascorbate has a molecular weight of 374.5 g/mol and each mole of magnesium ascorbate provides two moles of ascorbate. Accordingly, the 300 to 2000 mmol ascorbate anion per litre can be provided by 56.2 to 374.5 g/litre magnesium ascorbate.

Depending on the pH of the solution, some ascorbate anion may be protonated and thus exist as free ascorbic acid. At the pH of solutions that would typically be administered, only a very minor proportion of ascorbate is protonated. In calculations of concentrations of "ascorbate anion" herein, the concentration of "ascorbate anion" is taken as the total concentration of all ascorbate anion present, including the proportion that is protonated.

A solution of the invention comprises 50 to 450 g/litre of an ascorbate component, the ascorbate component being ascorbic acid, one or more salts of ascorbic acid or a mixture of ascorbic acid and one or more salts of ascorbic acid. For example, a solution of the invention comprises 50 to 300 g/litre of ascorbate component, for example 50 to 200 g/litre, for example 60 to 150 g/litre, for example 60 to 120 g/litre, for example 80 to 120 g/litre, for example 100 to 120 g/litre.

In an embodiment, the ascorbate component consists essentially of sodium ascorbate alone. For example, it may be present in an amount as mentioned immediately above.

In an alternative embodiment, the ascorbate component comprises (or consists essentially of) sodium ascorbate and ascorbic acid. For example, they may be present in a total amount as mentioned immediately above. They may be in a weight ratio of sodium ascorbate:ascorbic acid from 1:10 to 10:1, for example 2:8 to 8:2, for example 3:7 to 7:3, for example 1.4:1 to 1.8:1.

In an alternative embodiment, the ascorbate component comprises (or consists essentially of) of sodium ascorbate and magnesium ascorbate. For example, they may be present in a total amount as mentioned immediately above. They may be in a weight ratio of sodium ascorbate:magnesium ascorbate from 1:10 to 10:1, for example 2:8 to 8:2, for example 3:7 to 7:3, for example 1.8:1 to 1.4:1.

The cleansing solution comprises polyethylene glycol. The polyethylene glycol (PEG) may, for example, have an average molecular weight of 2000 to 8000, for example 2500 to 4500 Da, for example 3000 to 4000 Da. For example, the PEG may be PEG 3350 or PEG 4000 as defined in national pharmacopeias. Further examples of suitable PEGs recognized in some national pharmacopeias include Macrogols, for example Macrogol 3350 or Macrogol 4000.

The cleansing solution comprises 10 to 200 g per litre of PEG. Preferably, the solution comprises 10 to 160 g per litre of PEG, more preferably 10 to 120 g per litre, for example 20 to 100 g per litre, for example 30 to 90 g per litre, for example 40 g per litre or 80 g per litre.

The cleansing solution may additionally comprise one or more of:
c) one or more electrolytes;
d) one or more alkali metal or alkaline earth metal sulphates;
e) one or more flavouring agents;
f) one or more sweeteners.

The cleansing solution may comprise one or more electrolytes. Electrolytes include salts of sodium, potassium, calcium and magnesium, particularly sodium and potassium; and salts of chloride, iodide, bicarbonate and carbonate, particularly chloride. Preferred electrolytes are sodium chloride and potassium chloride. In an embodiment, the solution is substantially free from sodium bicarbonate.

For example, the solution may comprise sodium chloride at a concentration of 1 to 10 g per litre. For example, sodium chloride may be present at a concentration of 2 to 8 g per litre, for example 3 to 7 g per litre.

For example, the solution may comprise potassium chloride at a concentration of 1 to 10 g per litre. For example, potassium chloride may be present at a concentration of 1 to 8 g per litre, for example 1.5 to 6 g per litre, for example 2 to 5 g per litre.

In an embodiment, the solution comprises sodium chloride and potassium chloride. They can be present in the amounts mentioned immediately above. For example, sodium chloride may be present at a concentration of 3 to 7 g per litre and potassium chloride may be present at a concentration of 2 to 5 g per litre.

The cleansing solution may comprise one or more alkali metal sulphates, alkaline earth metal sulphates or a mixture thereof (herein referred to as a "sulphate component"). An alkali metal or alkaline earth metal sulphate may, for example, be selected from sodium sulphate, potassium sulphate and magnesium sulphate. The solution may comprise more than one of sodium sulphate, potassium sulphate and magnesium sulphate, for example all three. Preferably, the sulphate component is or includes sodium sulphate. In an embodiment, the solution does not comprise a sulphate component.

For example, the solution may comprise a sulphate component at a concentration of 2 to 20 g per litre, for example 5 to 15 g per litre, for example 8 to 15 g per litre, for example 10 to 14 g per litre, for example 12 g per litre. The one or more sulphate salts may be provided in any pharmaceutically acceptable form: they may each be anhydrous, or be in a hydrated form. The weights mentioned herein refer to the weight of the sulphate salt excluding any water of hydration.

In the solutions of the invention described herein, the quantities of the individual components recited do not include any solutes that may be present in the water used to prepare the solutions, for example, in hard water areas there may be significant amounts of $Ca^{2+}$ and $Mg^{2+}$ carbonates, bicarbonates or sulphates present in tap water.

The cleansing solution preferably includes a flavouring agent. A flavouring for use in compositions of the invention should preferably mask saltiness, be relatively sweet but not excessively so, and be stable in the composition. A flavouring makes the solutions more palatable and thus aids patient compliance. Preferred flavourings include lemon e.g. Ungerer Lemon (available from Ungerer Limited, Sealand Road, Chester, England CH1 4LP) strawberry e.g. Ungerer Strawberry, grapefruit e.g. Ungerer Grapefruit flavouring powder, blackcurrant e.g. Ungerer Blackcurrant, pineapple e.g. IFF (International Flavours and Fragrances) Pineapple flavouring powder and vanilla/lemon and lime e.g. IFF Vanilla and Givaudin Roure Lemon and Lime Flav-o-lok. Those and further suitable flavourings are available from International Flavours and Fragrances Inc. (Duddery Hill, Haverhill, Suffolk, CB9 8LG, England), Ungerer & Company (Sealand Road, Chester, England CH1 4LP) or Firmenich (Firmenich UK Ltd., Hayes Road, Southall, Middlesex UB2 5NN). More preferred flavourings are lemon, kiwi, strawberry and grapefruit.

The amount of flavouring required depends on the nature and strength of the flavouring in question. Typically, it is 0.05 to 2.0 g per litre.

The cleansing solution preferably includes a sweetener. Sugar-based sweeteners are generally not suited for colon cleansing compositions because the delivery of unabsorbed sugars to the colon provides a substrate for bacteria. Such sugars may be metabolised by the bacteria to form explosive gases such as hydrogen and methane. The presence of explosive gases in the colon can be highly dangerous when electrical apparatus is to be used during colonoscopy or other procedures. Preferred sweeteners include aspartame, acesulfame potassium (acesulfame K), sucralose and saccharine, and/or combinations thereof. For example, compositions of the invention may comprise one or both of aspartame and acesulfame potassium (acesulfame K). For example, compositions of the invention may comprise one or both of sucralose and acesulfame potassium (acesulfame K). Alternatively, compositions of the invention can be substantially free from added sweeteners, for example to minimize the number of different components in the compositions. Citric acid may also be present as a taste enhancer. Citric acid and/or salts thereof may replace some or all of the ascorbate in solutions of the invention.

The amount of sweetener required depends on the nature and strength of the sweetener being considered. Typically, it is 0.10 to 1.0 g per litre.

The invention thus provides a colon cleansing solution comprising:
a) 300 to 2000 mmol per litre ascorbate anion;
b) 10 to 200 g per litre PEG.
c) one or more electrolytes;
d) optionally one or more alkali metal or alkaline earth metal sulphates;
e) optionally one or more flavouring agents; and
f) optionally one or more sweeteners.

In particular, the invention provides a colon cleansing solution comprising (or consisting essentially of water and):
a) 300 to 2000 mmol per litre ascorbate anion;
b) 10 to 200 g per litre PEG having an average molecular weight of 3000 to 4000 Da;
c) sodium chloride and potassium chloride;
d) optionally sodium sulphate;
e) optionally one or more flavouring agents; and
f) optionally one or more sweeteners.

Each of c) and d) may be present in the concentrations described above. Each of e) and f) may be as described above and/or be in the concentrations described above.

In particular, the invention provides a colon cleansing solution comprising (or consisting essentially of water and):
a) 300 to 2000 mmol per litre ascorbate anion;
b) 10 to 200 g per litre PEG having an average molecular weight of 3000 to 4000 Da;
c) sodium chloride and potassium chloride;
e) one or more flavouring agents; and
f) one or more sweeteners.

In one embodiment, the one or more components of c), d) e) and f) are present in the solution. In an alternative presentation, some or all of components c), d) e) and f) may be provided separately from the solution, for example in a tablet or capsule. In an embodiment, the solution may comprise a) the ascorbate component and b) PEG, and optional flavouring and sweetener (e) and f)), and a tablet or capsule may comprise c) the one or more electrolytes and/or d) the one or more alkali metal or alkaline earth metal sulphates, again with optional flavouring and sweetener (e) and f)). The flavouring and sweeteners need not be the same in the tablet or capsule as in the solution.

In general it is not necessary for the solutions to include preservatives or anti-oxidants. Nevertheless, low levels of anti-oxidants or preservatives may be used if required.

Preferably, the colon cleansing solution is hyper-osmotic. That is to say that it has a higher osmotic strength than blood in the human body. It may, for example have a measured osmolality in the range 500 to 2000 mOsmol/kg. For example, the osmolality may be in the range 700 to 1800 mOsmol/kg, for example 800 to 1700 mOsmol/kg, for example 900 to 1600 mOsmol/kg, for example 900 to 1300 mOsmol/kg, for example 1000 to 1300 mOsmol/kg.

Osmolality can be measured in various ways. In general, either freezing point depression or vapour-pressure alteration is used. For example, an Advanced Instruments, Inc Model 3250 osmometer (a freezing point depression device) can be used. Vapour pressure measurement can also be used, for example using an ELITech Group Vapro 5600 device. Osmolality values cited herein are preferably taken to be values measured using a freezing point depression osmometer, for example using an Advanced Instruments, Inc Model 3250 osmometer following standard operating procedure.

When carrying out a bowel cleansing treatment, a subject typically takes a single dose or a split dose of cleansing solution. In a split-dose treatment, typically two doses are taken separated by a time interval, for example an overnight interval. Each dose in a split dose treatment is smaller than the dose in the single dose treatment. In a split dose treatment, the two doses may each have the same composition, or they may be different.

For a single dose treatment, the solution of the invention may be taken in a volume of 700 to 1500 ml. For example, the subject may take from 750 ml to 1300 ml of the solution, for example 800 to 1200 ml, for example 900 to 1100 ml, for example 1000 ml. In an embodiment, the subject may take some additional clear fluid. The additional clear fluid may be taken after taking the solution. Alternatively, the additional clear fluid may be co-administered with the intake of the solution of the invention. By "co-administered" is meant the coordinated administration of a solution of the invention with clear fluid.

For a split dose treatment, the solution of the invention may be taken with one of the doses having a volume of 200 to 1000 ml. For example, the subject may take 300 ml to 1000 ml of the solution, for example 300 ml to 900 ml, for example 300 ml to 800 ml, for example 400 ml to 700 ml, for example 400 to 600 ml, for example 450 to 550 ml, for example 500 ml. In an embodiment, the subject may take some additional clear fluid with each or either dose the solution of the invention. The additional clear fluid may be taken after taking a dose of the solution. Alternatively, the additional clear fluid may be co-administered with the intake of a dose of the solution of the invention.

In a split dose treatment, the solution of the invention may be taken for one or for both of the doses. Preferably, the solution of the invention is taken as the second solution. The first solution may then be a solution of different constitution from the second solution. Thus, in a preferred embodiment of a split dose bowel cleansing treatment, a subject takes a dose of an initial cleansing solution, optionally followed by some additional clear fluid. After an interval, the subject then takes a dose of the solution of the invention, optionally followed by some additional clear fluid.

The volume of clear fluid that a subject takes after the first or second dose may be in a range with a lower limit of 100 ml, 200 ml, 300 ml, 400 ml or 500 ml. Preferably, the lower limit is 300 ml, 400 ml or 500 ml. The volume may be in a range with an upper limit of 1200 ml, 1100 ml, 1000 ml, 900 ml or 800 ml. For example the volume may be in the range 100 ml to 1200 ml, for example 200 ml to 1100 ml, for example 300 ml to 1000 ml, for example 500 ml to 900 ml, for example 875 ml, for example 500 ml to 800 ml. The instructions provided to the subject may suggest that the additional clear fluid is ingested over a period of approximately one hour, for example in 150 to 200 ml fractions every 15 to 20 minutes. The additional clear fluid may be taken after taking a dose of the solution. Alternatively, the additional clear fluid may be co-administered with the intake of a dose of the solution of the invention.

A clear fluid for taking as the additional clear fluid, or for use as the clear fluid when making up a solution, may be any fluid that allows inspection of colonic output. The clear fluid should also not impede inspection of the colon during the colonoscopy. Typically the clear fluid is a water-based beverage, including, for example, water, lemonade, cola drinks, cordial drinks, clear fruit juices and even clear alcohol-containing beverages, for example beer. It is desirable that the clear fluid does not contain substantial amounts of or essentially any dietary fibre, as such fibre interferes with the cleansing of the colon according to the present invention. Accordingly, fruit juices, for example orange juice and kiwi juice, and fruit "squashes" should be strained before use. Clear fruit cordials, for example, lime cordial, are generally suitable. In view of the desirability of avoiding drinks containing glucose, so as to reduce the risk of explosive concentrations of hydrogen or methane building up in the gut, "diet" drinks containing no or low sugar are especially suitable, for example liquid drinks for diabetics, diet Coke®, diet lemonade, dietary carbonated drinks or dietary cordials.

The invention further provides a composition (for example a dry composition, for example a powder) for the preparation of a solution of the invention. A composition can be provided in a quantity for the preparation of a dose of the solution, for example a 500 ml dose. The invention provides a composition for admixture with water, wherein the composition is optionally presented in two or more parts and comprises:

a) 150 to 1000 mmol ascorbate anion provided by ascorbic acid, one or more salts of ascorbic acid, or a mixture thereof; and b) 5 to 100 g polyethylene glycol.

For example, the components may be in dry powder, granular or other dry form. They may alternatively be in the form of concentrates or slurries. Components may be in the same or different physical forms. For example, the composition is a dry composition, for example a dry powder composition. For example, one or both of components a) and b) are dry powders.

As set out above, the ascorbate anion may be provided by ascorbic acid, by one or more salts of ascorbic acid, or by a mixture of ascorbic acid and one or more salts of ascorbic acid. Preferred forms of the ascorbate component are as set out above in relation to solutions of the invention.

The composition of the invention preferably comprises ascorbate anion in an amount of: 150 to 750 mmol, for example 150 to 600 mmol, for example 150 to 500 mmol, for example 150 to 425 mmol, for example 175-400 mmol, for example 200-350 mmol.

Ascorbic acid has a molecular weight of 176 g/mol. Accordingly, the 150 to 1000 mmol ascorbate anion can be provided by 26.4 to 176 g ascorbic acid.

Sodium ascorbate has a molecular weight of 198 g/mol. Accordingly, the 150 to 1000 mmol ascorbate anion can be provided by 29.7 to 198 g sodium ascorbate.

Potassium ascorbate has a molecular weight of 214 g/mol. Accordingly, the 150 to 1000 mmol ascorbate anion can be provided by 32.1 to 214 g potassium ascorbate.

Magnesium ascorbate has a molecular weight of 374.5 g/mol and each mole of magnesium ascorbate provides two moles of ascorbate. Accordingly, the 150 to 1000 mmol ascorbate anion can be provided by 28.1 to 187.25 g magnesium ascorbate.

In solid form, ascorbic acid is typically made up of protonated free ascorbic acid. In calculations of concentrations of "ascorbate anion" herein, the number of moles of "ascorbate anion" is taken as the total concentration of all ascorbate anion present, including the proportion that is protonated.

The weight of the ascorbate component may be 20 to 220 g, for example 20 to 150 g, for example 20 to 100 g, for example 25 to 220 g, for example 25 to 150 g, for example 25 to 100 g, for example 25 to 75 g, for example 20 to 60 g, for example 50 to 60 g.

In an embodiment, the ascorbate component consists essentially of sodium ascorbate alone. For example, it may be present in an amount as mentioned immediately above.

In an alternative embodiment, the ascorbate component comprises (or consists essentially of) sodium ascorbate and ascorbic acid. For example, they may be present in a total amount as mentioned immediately above. They may be in a weight ratio of sodium ascorbate:ascorbic acid from 1:10 to 10:1, for example 2:8 to 8:2, for example 3:7 to 7:3, for example 1.4:1 to 1.8:1.

In an alternative embodiment, the ascorbate component comprises (or consists essentially of) sodium ascorbate and magnesium ascorbate. For example, they may be present in a total amount as mentioned immediately above. They may be in a weight ratio of sodium ascorbate:magnesium ascorbate from 1:10 to 10:1, for example 2:8 to 8:2, for example 3:7 to 7:3, for example 1.8:1 to 1.4:1.

Preferred forms of the PEG are as set out above in relation to solutions of the invention. The composition comprises 5 to 100 g of PEG. Preferably, the composition comprises 5 to 80 g of PEG, more preferably 5 to 60 g, for example 10 to 50 g, for example 15 to 45 g, for example 20 g or 40 g of PEG.

The composition may additionally comprise one or more of:

c) one or more electrolytes;
d) one or more alkali metal or alkaline earth metal sulphates;
e) one or more flavouring agents; and
f) one or more sweeteners.

Preferred electrolytes are as set out above in relation to solutions of the invention. For example, the composition may comprise sodium chloride in an amount of 0.5 to 5 g, for example 1 to 4 g, for example 1.5 to 3.5 g. For example, the composition may comprise potassium chloride in an amount of 0.5 to 5 g, for example 0.5 to 4 g, for example 0.75 to 3 g, for example 1.0 to 2.5 g.

Preferred alkali metal or alkaline earth metal sulphates are as set out above in relation to solutions of the invention. For example, the composition may comprise a sulphate component in an amount of 1 to 10 g, for example 2.5 to 7.5 g, for example 4 to 7.5 g, for example 5 to 7 g, for example 6 g. The one or more sulphate salts may be provided in any pharmaceutically acceptable form: they may each be anhydrous, or be in a hydrated form. The weights mentioned herein refer to the weight of the sulphate salt excluding any water of hydration.

Preferred flavouring agents are as set out above in relation to solutions of the invention. For example the amount of flavouring agent may be 0.025 to 1.0 g.

Preferred sweeteners are as set out above in relation to solutions of the invention. For example the amount of sweetener may be 0.05 to 0.5 g.

In particular, the invention provides a composition comprising (or consisting essentially of):
a) 150 to 1000 mmol ascorbate anion;
b) 5 to 100 g PEG having an average molecular weight of 3000 to 4000 Da.
c) sodium chloride and potassium chloride;
d) optionally sodium sulphate;
e) optionally one or more flavouring agents;
f) optionally one or more sweeteners.

Each of c) and d) may be present in the amounts described above. Each of e) and f) may be as described above and/or be in the amounts described above.

In one embodiment, the one or more components of c), d) e) and f) are present in the composition for making up a solution. In an alternative presentation, some or all of components c), d) e) and f) may be provided separately from the composition for making up the solution, for example in a tablet or capsule. In an embodiment, there may be provided the ascorbate component and PEG, and optional flavouring and sweetener, in a form for admixture with water, and a tablet or capsule comprising the one or more electrolytes and/or the one or more alkali metal or alkaline earth metal sulphates, again with optional flavouring and sweetener. The flavouring and sweeteners need not be the same in the tablet or capsule as in the composition for admixture with water.

In some embodiments, it is desirable to package the ascorbate and the PEG components separately from each other.

In an embodiment, the composition can be provided to the subject with a plurality of flavouring agents (each optionally with one or more sweeteners), each separately packaged. The subject can then select a preferred flavouring (or flavouring and sweetener combination) according to his or her taste. The subject also has the choice of not using any flavouring or sweetener at all.

In a further aspect, the invention provides a composition comprising the following components in the following weight ratios:
a) ascorbate 0.82 to 10.0 parts; and
b) polyethylene glycol 1.0 part.

As mentioned above, for example, the components may be in dry powder, granular or other dry form. They may alternatively be in the form of concentrates or slurries. Components may be in the same or different physical forms. For example, the composition is a dry composition, for example a dry powder composition. For example, one or both of components a) and b) are dry powders.

As set out above, the ascorbate anion may be provided by ascorbic acid, by one or more salts of ascorbic acid, or by a mixture of ascorbic acid and one or more salts of ascorbic acid. Preferred forms of the ascorbate component are as set out above in relation to solutions of the invention.

Preferred forms of the PEG are as set out above in relation to solutions of the invention. The composition of the invention preferably comprises ascorbate anion in a weight ratio to PEG of 0.82 to 5.0:1. More preferably, the weight ratio is 0.9 to 5.0:1, for example 1.0 to 4.0:1, for example 1.0 to 3.0:1, for example 1 to 2:1, or 2 to 3:1.

The composition may additionally comprise one or more of:
c) one or more electrolytes;
d) one or more alkali metal or alkaline earth metal sulphates;
e) one or more flavouring agents;
f) one or more sweeteners.

Preferred electrolytes are as set out above in relation to solutions of the invention. For example, the composition may comprise sodium chloride in a weight ratio to PEG of 0.005 to 1.0:1, for example 0.01 to 0.6:1, for example 0.03 to 0.5:1, for example 0.04 to 0.4:1, for example 0.05 to 0.3:1, for example 0.06 to 0.2:1. For example, the composition may comprise potassium chloride in a weight ratio to PEG of 0.005 to 1.0:1, for example 0.005 to 0.50:1, for example 0.01 to 0.50:1, for example 0.01 to 0.10:1, for example 0.02 to 0.08:1, for example 0.03 to 0.07:1.

For example, the invention provides a composition comprising the following components in the following weight ratios:
a) ascorbate anion: 0.82 to 10.0 parts;
b) polyethylene glycol: 1.0 part;
c1) sodium chloride: 0.005 to 1.0 parts; and
c2) potassium chloride: 0.005 to 1.0 parts.

The composition is preferably substantially free from sodium bicarbonate. For example, it is substantially free from any bicarbonate.

Preferred alkali metal or alkaline earth metal sulphates are as set out above in relation to solutions of the invention. For example, the composition may comprise a sulphate component (for example sodium sulphate) in a weight ratio to PEG of 0.01 to 0.50:1, For example, the composition may comprise a sulphate component (for example sodium sulphate) in a weight ratio to PEG of 0.02 to 0.25:1, for example 0.03 to 0.22:1, for example 0.05 to 0.20:1, for example 0.10 to 0.20:1.

Preferred flavouring agents are as set out above in relation to solutions of the invention. For example the composition may comprise a flavouring agent in a weight ratio to PEG of 0.0005 to 0.025:1, for example 0.001 to 0.025:1, for example 0.003 to 0.010:1.

Preferred sweeteners are as set out above in relation to solutions of the invention. For example the composition may comprise a sweetener in a weight ratio to PEG of 0.0005 to 0.025:1, for example 0.001 to 0.025:1, for example 0.002 to 0.010:1.

In particular, the invention provides a composition comprising (or consisting essentially of) the following components in the following weight ratios:
a) ascorbate anion: 0.82 to 10.0 parts
b) having an average molecular weight of 3000 to 4000 Da: 1.0 part.
c) sodium chloride and potassium chloride;
d) optionally sodium sulphate;
e) optionally one or more flavouring agents; and
f) optionally one or more sweeteners.

Each of c) and d) may be present in the weight ratios to PEG described above. Each of e) and f) may be as described above and/or be in the weight ratios to PEG described above.

Preferred compositions of the invention are dry compositions, for example dry powder compositions.

As mentioned above, the solutions of the invention find use in cleansing the colon. The invention thus provides, in a second aspect a solution in water of:

a) 300 to 2000 mmol per litre ascorbate anion provided by ascorbic acid, one or more salts of ascorbic acid, or a mixture thereof; and b) optionally 10 to 200 g per litre polyethylene glycol, for use in cleansing the colon of a mammal.

The solution for use in cleansing the colon of a mammal preferably comprises ascorbate anion in a concentration of: 300-1500 mmol per litre, for example 300-1200 mmol per litre, for example 300-1000 mmol per litre, for example 300-850 mmol per litre, for example 350-800 mmol per litre, for example 400-700 mmol per litre. As set out above, the ascorbate anion may be provided by ascorbic acid, by one or more salts of ascorbic acid, or by a mixture of ascorbic acid and one or more salts of ascorbic acid. Preferred forms of the ascorbate component are as set out above in relation to solutions of the invention.

In a preferred embodiment, PEG is present. Preferred forms of the PEG and preferred amounts thereof are as set out above in relation to solutions of the invention.

The solution for use in cleansing the colon of a mammal may additionally comprise one or more of:

c) one or more electrolytes;
d) one or more alkali metal or alkaline earth metal sulphates;
e) one or more flavouring agents;
f) one or more sweeteners.

Preferred electrolytes and preferred amounts thereof are as set out above in relation to solutions of the invention.

Preferred alkali metal or alkaline earth metal sulphates and preferred amounts thereof are as set out above in relation to solutions of the invention.

Preferred flavouring agents and preferred amounts thereof are as set out above in relation to solutions of the invention.

Preferred sweeteners and preferred amounts thereof are as set out above in relation to solutions of the invention.

For example, the solution in water comprises:
a) 150 to 1000 mmol ascorbate anion; and
b) optionally 5 to 100 g PEG.

In particular, the invention provides a solution comprising (or consisting essentially of water and):
a) 150 to 1000 mmol ascorbate anion;
b) 5 to 100 g PEG having an average molecular weight of 3000 to 4000 Da;
c) sodium chloride and potassium chloride;
d) optionally sodium sulphate;
e) optionally one or more flavouring agents; and
f) optionally one or more sweeteners for use in cleansing the colon of a mammal.

Each of c) and d) may be as described above and/or be present in the amounts described above in relation to solutions of the invention. Each of e) and f) may be as described above and/or be in the amounts described above.

As mentioned above, a bowel cleansing treatment typically involves a subject taking a single dose or a split dose of cleansing solution. The volume of solution that a subject takes in a single dose treatment is described hereinabove. The subject may take some additional clear fluid after taking the solution as described hereinabove.

The volume of solution that a subject takes in a split dose treatment is described hereinabove. The subject may take some additional clear fluid after each or either dose the solution as described hereinabove.

The solutions and compositions of the invention find particular use in split dose colon cleansing treatments in which the subject takes two different solutions: a first colon cleansing solution, followed by a second colon cleansing solution. Preferably, the solution of the invention is the second colon cleansing solution. Alternatively, it may be the first solution. The invention thus provides a method of cleansing the colon of a mammal comprising:

the subject taking an effective amount of a first colon cleansing solution;
the subject taking an effective amount of a second colon cleansing solution, the second colon cleansing solution being a solution comprising a) 300 to 2000 mmol per litre ascorbate; and
b) optionally 10 to 200 g per litre polyethylene glycol.

The method of the invention may be used to cleanse the colon prior to carrying out a diagnostic, therapeutic or surgical procedure on the colon, rectum or anus or elsewhere in the abdomen. The diagnostic or surgical procedure may, for example, be colonoscopy, barium enema examination, sigmoidoscopy or colon surgery. Preferably, the first solution is of different composition from the second.

The invention further provides a method of conducting a diagnostic or surgical procedure, for example, a colonoscopy, barium enema examination, sigmoidoscopy or colon surgery, comprising the steps of:

a) cleansing the colon by a method of the invention, and then
b) carrying out the diagnostic or surgical procedure.

The invention provides a kit comprising:
a first colon cleansing solution, and
a second colon cleansing solution, the second colon cleansing solution being a solution in water of:

a) 300 to 2000 mmol per litre ascorbate anion provided by ascorbic acid, one or more salts of ascorbic acid, or a mixture thereof; and
b) optionally 10 to 200 g per litre polyethylene glycol.

In an embodiment, the first solution is different from the second. The kit may comprise instructions for use.

The invention further provides a first colon solution, and a second colon solution, for use in a method of cleansing the colon comprising:

the subject taking an effective amount of a first colon cleansing solution;
the subject taking an effective amount of a second colon cleansing solution, the second colon cleansing solution being a solution in water of:

a) 300 to 2000 mmol per litre ascorbate anion provided by ascorbic acid, one or more salts of ascorbic acid, or a mixture thereof; and
b) optionally 10 to 200 g per litre polyethylene glycol.

In an embodiment, the first solution is different from the second.

The second colon cleansing solution is preferably as described hereinabove in relation to solutions and uses of the first aspect of the invention. It is preferably used in a volume as described hereinabove in relation to solutions and uses of the invention.

The first cleansing solution may, for example, be a bowel content suspending agent. The first cleansing solution may comprise polyethylene glycol and/or an alkali metal sulphate, an alkaline earth metal sulphate or a mixture thereof. The first cleansing solution may be hyper-osmotic.

Preferably, the first colon cleansing solution comprises polyethylene glycol (PEG). The polyethylene glycol (PEG) may have an average molecular weight of 2000 to 8000, for example 2500 to 4500 Da, for example 3000 to 4000 Da. For example, the PEG may be PEG 3350 or PEG 4000 as defined in national pharmacopeias. Further examples of suitable PEGs recognized in some national pharmacopeias include Macrogols, for example Macrogol 3350 or Macrogol 4000.

Preferably, the first colon cleansing solution comprises 70 to 250 g per litre of PEG. Preferably, the solution comprises 130 to 250 g per litre PEG, for example 90 to 200 g per litre of PEG, more preferably 100 to 200 g per litre, for example 120 to 150 g per litre, for example 133.3 g per litre.

Preferably, the first colon cleansing solution comprises one or more alkali metal sulphates, alkaline earth metal sulphates or a mixture thereof (herein referred to as a "sulphate component"). An alkali metal or alkaline earth metal sulphate may, for example, be selected from sodium sulphate, potassium sulphate and magnesium sulphate. The solution may comprise more than one of sodium sulphate, potassium sulphate and magnesium sulphate, for example all three. Preferably, the sulphate component is or includes sodium sulphate.

Preferably, the first colon cleansing solution comprises a sulphate component (for example sodium sulphate) at a concentration of 2 to 20 g per litre, for example 2 to 15 g per litre, for example 5 to 15 g per litre, for example 8 to 12 g per litre, for example 8 or 12 g per litre. For example, the first colon cleansing solution comprises 8.0 to 20 g per litre of one or more alkali metal sulphates, alkaline earth metal sulphates or a mixture thereof.

The first colon cleansing solution may comprise one or more electrolytes. Electrolytes include salts of sodium, potassium, calcium and magnesium, particularly sodium and potassium; and salts of chloride, iodide, bicarbonate and carbonate, particularly chloride. Preferred electrolytes are sodium chloride and potassium chloride. In an embodiment, sodium bicarbonate is not included.

For example, the first colon cleansing solution may comprise sodium chloride at a concentration of 0.5 to 5.0 g per litre. For example, sodium chloride may be present at a concentration of 1.0 to 4.0 g per litre, for example 1.0 to 3.0 g per litre, for example 1.5 to 3.0 g per litre, for example 2.0 to 3.0 g per litre.

For example, the first colon cleansing solution may comprise potassium chloride at a concentration of 1 to 10 g per litre. For example, potassium chloride may be present at a concentration of 0.05 to 5.0 g per litre, for example 0.1 to 3.0 g per litre, for example 0.2 to 2.0 g per litre, for example 0.5 to 1.5 g per litre, for example 0.5 to 1.1 g per litre.

In an embodiment, the first colon cleansing solution comprises sodium chloride and potassium chloride. They can be present in the amounts mentioned immediately above. For example, sodium chloride may be present at a concentration of 1.5 to 3.0 g per litre and potassium chloride may be present at a concentration of 0.2 to 2.0 g per litre.

The first colon cleansing solution preferably includes a flavouring agent. The first colon cleansing solution preferably includes a sweetener. Flavouring agents and sweeteners may be as described hereinabove.

In an embodiment, the first colon cleansing solution may be a solution as commercialised under the tradename MOVIPREP®.

Accordingly, the first colon cleansing solution in a kit of the invention comprises (or consists essentially of water and):
(i) 70 to 250 g per litre PEG having an average molecular weight of 2500 to 4500 Da.
(ii) 2.0 to 20 g per litre of one or more alkali metal sulphates, alkaline earth metal sulphates or a mixture thereof
(iii) optionally one or more electrolytes;
(iv) optionally one or more flavouring agents; and
(v) optionally one or more sweeteners.

For example, the first colon cleansing solution in a kit of the invention comprises (or consists essentially of water and):
(i) 90 to 200 g per litre PEG having an average molecular weight of 2500 to 4500 Da.
(ii) 2.0 to 15 g per litre of one or more alkali metal sulphates, alkaline earth metal sulphates or a mixture thereof
(iii) 0.5 to 5.0 g per litre sodium chloride, and 0.05 to 5.0 g per litre potassium chloride;
(iv) optionally one or more flavouring agents; and
(v) optionally one or more sweeteners.

The invention further provides, according to a third aspect, a colon cleansing solution comprising (or consisting essentially of water and):
(i) 130 to 250 g per litre PEG having an average molecular weight of 2500 to 4500 Da; (ii) 8.0 to 20 g per litre of one or more alkali metal sulphates, alkaline earth metal sulphates or a mixture thereof;
(iii 1) optionally 1.0 to 3.0 g per litre sodium chloride;
(iii 2) optionally 0.5 to 1.5 (for example 0.5 to 1.1) g per litre potassium chloride;
(iv) optionally one or more flavouring agents; and
(v) optionally one or more sweeteners.

There is also provided a composition for the preparation of such a solution, for example by admixture with water. Preferred amounts of each of components (i) to (v) in the solutions and compositions of the third aspect of the invention are as set out for the first colon cleansing solutions and first colon cleansing compositions hereinabove and hereinbelow.

In an embodiment, the first colon cleansing solution is provided in a volume of from 300 ml up to 1200 ml. For example, the first solution may have a volume in a range with a lower limit of 300 ml, 400 ml, 500 ml, 600 ml or 700 ml. Preferably, the lower limit is 500 ml, 600 ml or 700 ml. The volume may be in a range with an upper limit of 1200 ml, 1100 ml, 1000 ml, 900 ml or 800 ml. For example the volume may be in the range 400 ml to 1100 ml, for example 500 ml to 1000 ml, for example 600 ml to 900 ml, for example 700 ml to 800 ml. For example, the first colon cleansing solution is provided in a volume of 750 ml. The most appropriate volume will depend on the exact components of the solution and the amounts in which they are present. In general, for a solution of higher osmotic strength, a smaller volume will be required.

The first cleansing solution may, for example, have a measured osmolality in the range 200 to 1500 mOsmol/kg. In a preferred embodiment, it is hyper-osmotic. It may, for example have a measured osmolality in the range 320 to 1500 mOsmol. For example, the measured osmolality of the first cleansing solution is in the range 330 to 1200 mOsmol/kg, for example 340 to 1000 mOsmol/kg, for example 350 to 800 mOsmol/kg, for example 350 to 700 mOsmol/kg.

A colon cleansing solution according to the third aspect of the invention may be used together with a solution of the first aspect of the invention. Alternatively, it may be used in combination with a different other colon cleansing solution, or used in a suitable volume on its own. If used on its own, it may be used in a single dose or in a split dose administration. The invention provides a method of cleansing the colon of a subject comprising administering a solution of the third aspect of the invention. The solution may be administered on its own or in combination with a further, different, solution.

The invention further provides a kit comprising:

A) a first component, being a composition for the preparation of a first colon cleansing solution as described immediately above by admixture with water; and B) a second component, being a composition for the preparation of a second colon cleansing solution by admixture with water, the second colon cleansing solution being a solution as described hereinabove in relation to solutions and uses of the first aspect of the invention, Preferably, the kit further comprises instructions for use.

For example, components A) and B) may be in dry powder, granular or other dry form. They may alternatively be in the form of concentrates or slurries. Components A) and B) may be in the same or different physical forms. Components within A) and B) may be in the same or different physical forms. For example, one or both of components A) and B) are dry powders. A portion of either or each of components A) and B) may be in the form of one or more solid tablets or capsules.

For example, a kit of the invention may comprise
A) a first component, being a composition for the preparation of a first colon cleansing solution comprising (or consisting essentially of water and):
(i) 70 to 250 g per litre PEG having an average molecular weight of 2500 to 4500 Da.
(ii) 2 to 20 g per litre of one or more alkali metal sulphates, alkaline earth metal sulphates or a mixture thereof
(iii) optionally one or more electrolytes;
(iv) optionally one or more flavouring agents;
(v) optionally one or more sweeteners, and
B) a second component, being a composition optionally presented in two or more parts for the preparation of a second colon cleansing solution, comprising
a) 300 to 2000 mmol per litre ascorbate anion provided by ascorbic acid, one or more salts of ascorbic acid, or a mixture thereof; and
b) optionally 10 to 200 g per litre polyethylene glycol.

Preferably, the first solution is of different composition from the second. The concentrations of the components given here are the concentrations attained when the compositions are mixed with water according to the instructions provided with the kit.

The first colon cleansing solution may be used in a volume as described hereinabove, for example 300 ml to 1200 ml, for example 600 ml to 900 ml, for example 750 ml. The second colon cleansing solution may be used in a volume as described hereinabove, for example 600 ml to 900 ml, for example 750 ml. The second colon cleansing solution may be used in a volume as described hereinabove, for example 250 ml up to 1000 ml, for example 400 ml to 700 ml, for example 500 ml. Instructions comprised in the kit may instruct the user to prepare a solution by adding water to the required volume, for example a volume as mentioned in this paragraph.

Accordingly, a kit of the invention may comprise:
A) a first component, being a composition for the preparation of a first colon cleansing solution comprising (or consisting essentially of):
(i) 52.5 to 187.5 g PEG having an average molecular weight of 2500 to 4500 Da.
(ii) 1.5 to 15 g of one or more alkali metal sulphates, alkaline earth metal sulphates or a mixture thereof
(iii) optionally one or more electrolytes;
(iv) optionally one or more flavouring agents;
(v) optionally one or more sweeteners, and
B) a second component, being a composition optionally presented in two or more parts for the preparation of a second colon cleansing solution, comprising
a) 150 to 1000 mmol ascorbate anion; and
b) optionally 5 to 100 g polyethylene glycol, the first solution being different from the second.

The first component preferably comprises 97.5 to 187.5 g of PEG, for example 67.5 to 150 g of PEG, more preferably 75 to 150 g, for example 90 to 112.5 g, for example 100 g PEG.

Preferably, the first component comprises a sulphate component (for example sodium sulphate) in an amount of 1.5 to 11.25 g, for example 3.75 to 11.25 g, for example 6 to 9 g, for example 6 or 9 g. For example, the first component comprises 6.0 to 15 g of one or more alkali metal sulphates, alkaline earth metal sulphates or a mixture thereof.

Preferably, the first component comprises sodium chloride in an amount of 0.375 to 3.75 g. For example, sodium chloride may be present in an amount of 0.75 to 3.0 g, for example 0.75 to 2.25 g, for example 1.125 to 2.25 g, for example 1.5 to 2.25 g.

For example, the first component comprises potassium chloride in an amount of 0.75 to 7.5 g. For example, potassium chloride may be present in an amount of 0.0375 to 3.75 g, for example 0.075 to 2.25 g, for example 0.15 to 1.5 g, for example 0.375 to 1.125 g, for example 0.375 to 0.825 g.

In an embodiment, the first component comprises sodium chloride and potassium chloride. They can be present in the amounts mentioned immediately above. For example, sodium chloride may be present in an amount of 1.125 to 2.25 g and potassium chloride may be present in an amount of 0.15 to 1.5 g.

The second component of the kit of compositions of the invention is preferably a composition for the preparation of a solution of the first aspect of the invention as described herein above.

In an embodiment, a kit of the invention has instructions that instruct the user of the volume to which each component is to be made up with water. For example, the specified volume of water for each solution is less than one litre. For example, the specified volume for the first component may be 300 ml to 1200 ml, for example 600 ml to 900 ml, for example 750 ml. For example, the specified volume for the second component may be from 250 ml to 1000 ml, for example 400 ml to 700 ml, for example 500 ml. Further volumes that may be specified in the instructions are the volumes set out hereinabove in relation to the methods of the invention.

In general, the instructions specify that the first and second solutions are to be ingested in succession with a time interval between them. In an embodiment, the instructions specify that the first cleansing solution is ingested first followed, after time interval (for example the time between an evening and the following morning), by ingestion of the second cleansing solution.

It is convenient for the patient for a kit of the invention to be provided in the form of, for example, a box. In a kit of the invention the first and/or second components may each contained in one or more containers. In particular, the second component may be contained in more than one container. For example, if the second component comprises both ascorbic acid and PEG then the ascorbic acid and PEG may be contained in separate containers. The other constituents of the second component (for example one or more of sodium chloride, potassium chloride and sodium sulphate)

may be in either of the separate containers. For example, they may be in the container containing the PEG.

If a flavouring component is present in the first or second solution, then in a kit of the invention, the flavouring component for the relevant solution may be provided in a separate container from the other constituents of that solution.

Examples of suitable containers include tubs, bags and sachets. A preferred container is a sachet.

In one embodiment, a kit comprises:
A) a first sachet comprising a first composition for the preparation of the first cleansing solution;
B1) a second sachet;
B2) a third sachet;
wherein the second and third sachets together provide a composition for the preparation of the second cleansing solution.

For example, in a kit of the invention as mentioned immediately above:
A) the first sachet comprises polyethylene glycol and/or sodium sulphate;
B1) the second sachet comprises one or more components selected from polyethylene glycol, one or more alkali metal sulphates, alkaline earth metal sulphates or a mixture thereof, electrolytes and/or one or more salts of ascorbic acid; and
B2) the third sachet comprises ascorbic acid;
the one or more salts of ascorbic acid in the second sachet (B1) and the ascorbic acid in the third sachet (B2) together providing 300 to 2000 mmol per litre ascorbate anion.

For example, in a kit of the invention as mentioned immediately above:
A) the first sachet comprises:
(i) 70 to 250 g per litre PEG having an average molecular weight of 2500 to 4500 Da.
(ii) 2 to 20 g per litre of one or more alkali metal sulphates, alkaline earth metal sulphates or a mixture thereof
(iii) optionally one or more electrolytes;
(iv) optionally one or more flavouring agents; and
(v) optionally one or more sweeteners,
B1) the second sachet comprises:
(i) 10 to 200 g per litre polyethylene glycol,
(ii) optionally one or more alkali metal sulphates, alkaline earth metal sulphates or a mixture thereof,
   (iii) electrolytes; and
   (iv) or one or more salts of ascorbic acid; and
B2) the third sachet comprises ascorbic acid, the one or more salts of ascorbic acid in the second sachet (B1) and the ascorbic acid in the third sachet (B2) together providing 300 to 2000 mmol per litre ascorbate anion.

For example, in a kit of the invention:
A) the first sachet comprises:
(i) 52.5 to 187.5 g PEG having an average molecular weight of 2500 to 4500 Da.
(ii) 1.5 to 15 g of one or more alkali metal sulphates, alkaline earth metal sulphates or a mixture thereof
(iii) optionally one or more electrolytes;
(iv) optionally one or more flavouring agents;
(v) optionally one or more sweeteners,
B1) the second sachet comprises:
(i) 5 to 100 g PEG having an average molecular weight of 2500 to 4500 Da,
(ii) optionally one or more alkali metal sulphates, alkaline earth metal sulphates or a mixture thereof,
(iii) electrolytes and/or one or more salts of ascorbic acid; and
B2) the third sachet comprises ascorbic acid,
the one or more salts of ascorbic acid in the second sachet (B1) and the ascorbic acid in the third sachet (B2) together providing 150 to 1000 mmol ascorbate anion.

For example, in a further embodiment of a kit of the invention, rather than being provided within a first sachet (A) with the PEG, some or all of the sulphate(s), electrolytes, flavouring agents and sweeteners are provided in the form of a tablet or capsule. In a further embodiment of a kit of the invention, rather than being provided within a second or third sachet (B1 or B2) with the PEG, ascorbic acid or ascorbate component, some or all of the sulphate(s), electrolytes, flavouring agents and sweeteners are provided in the form of a tablet or capsule.

A kit may contain one treatment, for example a cleansing treatment, or several treatments. A treatment generally comprises one dose of the first cleansing solution (or components for preparing the first cleansing solution) and one dose of the second cleansing solution (or components for preparing the first cleansing solution). In a kit of the invention, preferably the first component comprises one dose of the first cleansing solution, and the second component comprises one dose of the second cleansing solution.

A kit of the invention may be for use in a method of cleansing the colon comprising:
   the subject taking an effective amount of a first colon cleansing solution as described herein;
   the subject taking an effective amount of a second colon cleansing solution as described herein.

The invention further provides a method of cleansing the colon comprising:
   the subject taking an effective amount of a first colon cleansing solution as described herein;
   the subject taking an effective amount of a second colon cleansing solution as described herein.

In the method, there is typically a time interval between taking the first solution and taking the second solution. Generally, the time interval is at least 4 hours, for example 6 hours or more, for example 8 hours or more. Typically, the time interval is less than 15 hours. The time interval between starting to take the first cleansing solution and starting to take the second cleansing solution may be, for example, the time between an evening and the following morning, for example 12 to 16 hours, for example 14 hours. For example, the subject may sleep (for example overnight) between taking the first and second cleansing solutions.

In a fourth aspect, the invention provides a method of cleansing the colon of a subject comprising:
   administering to the subject an effective amount of a first cleansing solution; and then after a time interval
   administering to the subject an effective amount of a second cleansing solution,
wherein the second cleansing solution is hyper-osmotic and contains ascorbic acid, one or more salts of ascorbic acid, or a mixture thereof; and wherein the first cleansing solution is either substantially free from ascorbic acid and salts thereof, or contains ascorbic acid, one or more salts of ascorbic acid, or a mixture thereof, in an amount providing a lower concentration of ascorbate anion than is present in the second cleansing solution.

For example, the invention provides a method of cleansing the colon of a subject comprising:
   the subject taking an effective amount of a first cleansing solution; and then after a time interval
   the subject taking an effective amount of a second cleansing solution,
wherein the second cleansing solution is hyper-osmotic and contains ascorbic acid, one or more salts of ascorbic acid, or a mixture thereof; and wherein the first cleansing solution is either substantially free from ascorbic acid and salts thereof, or contains ascorbic acid, one or more salts of ascorbic acid, or a mixture thereof, in an amount providing a lower concentration of ascorbate anion than is present in the second cleansing solution.

The amount of solution that constitutes an "effective amount" need not be the same for the first and second solutions.

The method provides satisfactory cleansing of the colon whilst not being wasteful of ascorbic acid component in the first cleansing solution. In addition, the method of the invention provides satisfactory cleansing of the colon with ingestion of a smaller total volume of the solutions than in the prior art. The first cleansing solution is preferably a bowel content suspending agent. The second cleansing solution is a bowel motility agent.

The invention also provides a kit comprising:
 a first colon cleansing solution; and
 a second colon cleansing solution,
wherein the second colon cleansing solution is hyper-osmotic and contains ascorbic acid, one or more salts of ascorbic acid, or a mixture thereof; and wherein the first colon cleansing solution is either substantially free from ascorbic acid and salts thereof, or contains ascorbic acid, one or more salts of ascorbic acid, or a mixture thereof, in an amount providing a lower concentration of ascorbate anion in the first colon solution than is present in the second colon cleansing solution.

In some embodiments of the method of the fourth aspect of the invention, the stool output immediately after the ingestion of the first solution may be less copious than after ingestion of the second solution. Given that the subject will often wish to sleep between taking the first bowel cleansing solution and the second solution, it may be advantageous in certain instances for the first cleansing solution to result in a slightly lower stool output than the second cleansing solution.

The invention also provides a kit comprising:
a) a first component, being a composition for the preparation of a first colon cleansing solution by admixture with a clear fluid (for example water); and
b) a second component, being a composition for the preparation of a second colon cleansing solution by admixture with a clear fluid (for example water),
and optionally instructions for use that specify the volume to which each component is to be made up with a clear fluid (for example water),
wherein the second colon cleansing solution, when made up to the instructed specified volume with the clear fluid (for example water), is hyper-osmotic and contains ascorbic acid, one or more salts of ascorbic acid, or a mixture thereof; and wherein the first colon cleansing solution is either substantially free from ascorbic acid and salts thereof, or contains, when made up to the instructed specified volume with the clear fluid (for example water), ascorbic acid, one or more salts of ascorbic acid, or a mixture thereof, in an amount providing a lower concentration of ascorbate anion in the first colon solution than in the second colon cleansing solution.

In an embodiment, the invention provides a method of cleansing the colon of a subject comprising:
 administering to the subject an effective amount of a first cleansing solution; and then after a time interval
 administering to the subject an effective amount of a second cleansing solution,
wherein the first cleansing solution contains polyethylene glycol (PEG) and is hyper-osmotic; and wherein the second cleansing solution contains polyethylene glycol (PEG) and is more hyper-osmotic than the first cleansing solution.

For example, the invention provides a method of cleansing the colon of a subject comprising:
 the subject taking an effective amount of a first cleansing solution; and then after a time interval
 the subject taking an effective amount of a second cleansing solution,
wherein the first cleansing solution contains polyethylene glycol (PEG) and is hyper-osmotic; and wherein the second cleansing solution contains polyethylene glycol (PEG) and is more hyper-osmotic than the first cleansing solution.

Osmolality can be measured in various ways. In general, either freezing point depression or vapour-pressure alteration is used. For example, an Advanced Instruments, Inc Model 3250 osmometer (a freezing point depression device) can be used. Vapour pressure measurement can also be used, for example using an ELITech Group Vapro 5600 device. Osmolality values cited herein are preferably taken to be values measured using a freezing point depression osmometer, for example using an Advanced Instruments, Inc Model 3250 osmometer following standard operating procedure.

The amount of solution that constitutes an "effective amount" need not be the same for the first and second solutions.

The method of the invention provides satisfactory cleansing of the colon with ingestion of a smaller total volume of the solutions than in the prior art. The reduced volume requirement helps to improve patient compliance.

For example, the second cleansing solution may comprise ascorbic acid, one or more salts of ascorbic acid, or a mixture thereof. In solution, ascorbic acid and salts thereof provide ascorbate anion. Depending on the pH of the solution, some ascorbate anion is protonated and thus exists as free ascorbic acid. At the pH of solutions that would typically be administered, only a very minor proportion of ascorbate is protonated. In calculations of concentrations of "ascorbate anion" herein, the concentration of "ascorbate anion" is taken as the total concentration of all ascorbate anion present, including the proportion that is protonated. Ascorbic acid or salts thereof, contribute to the osmotic load, along with other solutes. In one embodiment, the first cleansing solution does not contain ascorbic acid or a salt thereof. Alternatively, the first solution may contain ascorbic acid, one or more salts of ascorbic acid, or a mixture thereof. Typically, if the first solution contains ascorbic acid, one or more salts of ascorbic acid, or a mixture thereof, it contains them in an amount providing a lower concentration of ascorbate anion than is present in the second cleansing solution.

The invention also provides a kit comprising:
 a first colon cleansing solution; and
 a second colon cleansing solution,
wherein the first cleansing solution contains polyethylene glycol (PEG) and is hyper-osmotic; and wherein the second cleansing solution contains polyethylene glycol (PEG) and is more hyper-osmotic than the first cleansing solution.

The invention also provides a kit comprising:
a) a first component, being a composition for the preparation of a first colon cleansing solution by admixture with a clear fluid (for example water); and
b) a second component, being a composition for the preparation of a second colon cleansing solution by admixture with a clear fluid (for example water), and instructions for use that specify the volume to which each component is to be made up with a clear fluid (for example water),
wherein the first cleansing solution contains polyethylene glycol (PEG) and, when made up to the instructed specified volume with the clear fluid (for example water), is hyper-osmotic; and wherein the second cleansing solution contains polyethylene glycol (PEG) and, when made up to the instructed specified volume with the clear fluid (for example water), is more hyper-osmotic than the first cleansing solution.

For example, components a) and b) may be in dry powder, granular or other dry form. They may alternatively be in the form of concentrates or slurries. Components a) and b) may be in the same or different physical forms. Components within a) and b) may be in the same or different physical forms. For example, one or both of components a) and b) are dry powders.

In an embodiment, the invention provides a method of cleansing the colon of a subject comprising:
administering to the subject an effective amount of a first cleansing solution; and then after a time interval
administering to the subject an effective amount of a second cleansing solution,
wherein the first cleansing solution and the second cleansing solution are different, and wherein the first cleansing solution contains an alkali metal sulphate, an alkaline earth metal sulphate or a mixture thereof; and the second cleansing solution contains ascorbic acid, one or more salts of ascorbic acid, or a mixture thereof.

The amount of solution that constitutes an "effective amount" need not be the same for the first and second solutions.

The first cleansing solution may contain polyethylene glycol (PEG). When made up to the instructed specified volume with water, it is preferably hyper-osmotic. The second cleansing solution may contain polyethylene glycol (PEG). When made up to the instructed specified volume with water, it may be hyper-osmotic, preferably more hyper-osmotic than the first cleansing solution.

Typically, if the first solution contains ascorbic acid, one or more salts of ascorbic acid, or a mixture thereof, it contains them in an amount providing a lower concentration of ascorbate anion than is present in the second cleansing solution. In an embodiment, the first cleansing solution does not contain ascorbic acid, one or more salts of ascorbic acid, or a mixture thereof. Typically, if the second solution contains an alkali metal sulphate, an alkaline earth metal sulphate or a mixture thereof it contains them in an amount providing a lower concentration of sulphate anion than is present in the first cleansing solution. In an embodiment, the second cleansing solution does not contain an alkali metal sulphate, an alkaline earth metal sulphate or a mixture thereof.

For example, the invention provides a method of cleansing the colon of a subject comprising:
the subject taking an effective amount of a first cleansing solution; and then after a time interval
the subject taking an effective amount of a second cleansing solution,
wherein the first cleansing solution and the second cleansing solution are different, and wherein the first cleansing solution contains an alkali metal sulphate, an alkaline earth metal sulphate or a mixture thereof; and the second cleansing solution contains ascorbic acid, one or more salts of ascorbic acid, or a mixture thereof.

The amount of solution that constitutes an "effective amount" need not be the same for the first and second solutions.

The method of the invention provides satisfactory cleansing of the colon with ingestion of a smaller total volume of the solutions than in the prior art. The reduced volume requirement helps to improve patient compliance.

For example, the second cleansing solution may comprise ascorbic acid, one or more salts of ascorbic acid, or a mixture thereof. In solution, ascorbic acid and salts thereof provide ascorbate anion. Ascorbic acid or salts thereof, contribute to the osmotic load, along with other solutes. In one embodiment, the first cleansing solution does not contain ascorbic acid or a salt thereof. Alternatively, the first solution may contain ascorbic acid, one or more salts of ascorbic acid, or a mixture thereof. Typically, if the first solution contains ascorbic acid, one or more salts of ascorbic acid, or a mixture thereof, it contains them in an amount providing a lower concentration of ascorbate anion than is present in the second solution.

The invention also provides a kit comprising:
a first colon cleansing solution; and
a second colon cleansing solution,
wherein the first cleansing solution and the second cleansing solution are different, and wherein the first cleansing solution contains an alkali metal sulphate, an alkaline earth metal sulphate or a mixture thereof; and the second cleansing solution contains ascorbic acid, one or more salts of ascorbic acid, or a mixture thereof.

The first cleansing solution may contain polyethylene glycol (PEG). When made up to the instructed specified volume with water, it is preferably hyper-osmotic. The second cleansing solution may contain polyethylene glycol (PEG). When made up to the instructed specified volume with water, it may be hyper-osmotic, preferably more hyper-osmotic than the first cleansing solution.

The invention also provides a kit comprising:
a) a first component, being a composition for the preparation of a first colon cleansing solution by admixture with a clear fluid (for example water); and
b) a second component, being a composition for the preparation of a second colon cleansing solution by admixture with a clear fluid (for example water),
and instructions for use that specify the volume to which each component is to be made up with a clear fluid (for example water),
wherein the first cleansing solution and the second cleansing solution are different, and wherein the first cleansing solution contains an alkali metal sulphate, an alkaline earth metal sulphate or a mixture thereof; and the second cleansing solution contains ascorbic acid, one or more salts of ascorbic acid, or a mixture thereof.

For example, components a) and b) may be in dry powder, granular or other dry form. They may alternatively be in the form of concentrates or slurries. Components a) and b) may be in the same or different physical forms. Components within a) and b) may be in the same or different physical forms. For example, one or both of components a) and b) are dry powders.

In a further embodiment, the invention provides a method of cleansing the colon of a subject comprising:
administering to the subject an effective amount of a first cleansing solution; and then after a time interval
administering to the subject an effective amount of a second cleansing solution, wherein the first cleansing solution and the second cleansing solution are different and, together, comprise the components:
a) 80 to 250 g of a polyethylene glycol;
b) 10 to 150 g of ascorbic acid, one or more salts of ascorbic acid or a mixture of ascorbic acid and one or more salts of ascorbic acid (the "ascorbate component");
c) 1 to 15 g of an alkali metal or alkaline earth metal sulphate or a mixture of alkali metal or alkaline earth metal sulphates (the "sulphate component");
d) 1 to 15 g of electrolytes;
e) optionally one or more sweeteners, and
f) optionally one or more flavourings
wherein the sulphate component is in the first cleansing solution and the ascorbate component is in the second cleansing solution.

The amount of solution that constitutes an "effective amount" need not be the same for the first and second solutions.

The invention further provides a kit comprising two or more compositions for separate admixture with a clear fluid (for example water) wherein the compositions together comprise the components:
a) 80 to 250 g of a polyethylene glycol;
b) 10 to 150 g of ascorbic acid, one or more salts of ascorbic acid or a mixture of ascorbic acid and one or more salts of ascorbic acid (the "ascorbate component");
c) 1 to 15 g of an alkali metal or alkaline earth metal sulphate or a mixture of alkali metal or alkaline earth metal sulphates (the "sulphate component");
d) 1 to 15 g of electrolytes;
e) optionally one or more sweeteners;
f) optionally one or more flavourings
wherein the components are arranged such that the sulphate component is in a first dry composition and the ascorbate component is in second dry composition.

For example, the components of the two or more compositions may be in dry powder, granular or other dry form. They may alternatively be in the form of concentrates or slurries. The two or more compositions may be in the same or different physical forms. Components within each of the two or more compositions may be in the same or different physical forms. For example, one or both of the compositions is a dry powder. The clear fluid may be the same or different for the two or more compositions.

The invention further provides a kit comprising two or more solutions wherein the solutions together comprise the components:
a) 80 to 250 g of a polyethylene glycol;
b) 10 to 150 g of ascorbic acid, one or more salts of ascorbic acid or a mixture of ascorbic acid and one or more salts of ascorbic acid (the "ascorbate component");
c) 1 to 15 g of an alkali metal or alkaline earth metal sulphate or a mixture of alkali metal or alkaline earth metal sulphates (the "sulphate component");
d) 1 to 15 g of electrolytes;
e) optionally one or more sweeteners;
f) optionally one or more flavourings
wherein the components are arranged such that the sulphate component is in a first solution and the ascorbate component is in second solution.

For example, each of the first and second compositions (or solutions) may contain some of the electrolytes of component d). For example, each of the first and second compositions (or solutions) may contain some of the polyethylene glycol of component a). Alternatively, the polyethylene glycol of component a) may be contained only in the first composition (or solution). For example, each of the first and second compositions (or solutions) may contain some of the sweetener of component e). For example, each of the first and second compositions (or solutions) may contain some of the flavouring of component f). The first composition (or solution) may contain more of component e) or f) than the second composition (or solution).

In an alternative embodiment, a method, solution or kit is provided wherein the first cleansing solution and the second cleansing solution have different compositions and, together, comprise the components:
a) 80 to 250 g of a polyethylene glycol;
b) 10 to 150 g of ascorbic acid, one or more salts of ascorbic acid or a mixture of ascorbic acid and one or more salts of ascorbic acid (the "ascorbate component");
c) 1 to 15 g of an alkali metal or alkaline earth metal sulphate or a mixture of alkali metal or alkaline earth metal sulphates (the "sulphate component");
d) 1 to 15 g of electrolytes;
e) optionally one or more sweeteners, and
f) optionally one or more flavourings;
wherein the pair of solutions is not a combination in which: the first solution contains 100 g PEG3350, 3 g $Na_2SO_4$, 1.4 g NaCl and 0.3 g KCl; or the first solution contains 100 g PEG3350, 6 g $Na_2SO_4$, 1.6 g NaCl and 0.7 g KCl; or the first solution contains 100 g PEG3350, 9 g $Na_2SO_4$, 2.0 g NaCl and 1.0 g KCl; and
the second solution contains 40 g PEG3350, 3.5 g NaCl, 2.2 g KCl and 56.6 g sodium ascorbate; or the second solution contains 20 g PEG3350, 2.7 g NaCl, 1.3 g KCl, 33.9 g sodium ascorbate and 20.1 g ascorbic acid; or the second solution contains 40 g PEG3350, 2.8 g NaCl, 3.1 g KCl 33.9 g sodium ascorbate and 20.1 g ascorbic acid; or the second solution contains 40 g PEG3350, 6 g $Na_2SO_4$, 2.8 g NaCl, 2.0 g KCl and 33.9 g sodium ascorbate; or the second solution contains 40 g PEG3350, 3.1 g NaCl, 1.3 g KCl, 33.9 g sodium ascorbate and 21.4 g magnesium ascorbate.

The combined volume of the first and second cleansing solutions is preferably less than 2 litres. Preferably, it is 1750 ml or less, for example 1500 ml or less, for example 1250 ml or less. For most adult subjects, a combined volume of more than 500 ml is used, for example more than 750 ml. For example, a combined volume of from 500 ml to 1750 ml is used, for example from 750 ml to 1500 ml, for example from 1000 ml to 1500 ml, for example 1250 ml. For example the first cleansing solution may have a volume of 750 ml and the second cleansing solution may have a volume of 500 ml.

In an embodiment, the subject may take some additional clear fluid after taking the first cleansing solution but before taking the second cleansing solution; and/or after taking the second cleansing solution. In an embodiment, the total amount of additional clear fluid that the subject takes is in the range 1000 ml to 2500 ml, for example 1750 ml.

A clear fluid for taking as the additional clear fluid, or for use as the clear fluid when making up a solution, may be any fluid that allows inspection of colonic output. The clear fluid should also not impede inspection of the colon during the colonoscopy. Typically the clear fluid is a water-based beverage, including, for example, water, lemonade, cola drinks, cordial drinks, clear fruit juices and even clear alcohol-containing beverages, for example beer. It is desirable that the clear fluid does not contain substantial amounts of or essentially any dietary fibre, as such fibre interferes with the cleansing of the colon according to the present invention. Accordingly, fruit juices, for example orange juice and kiwi juice, and fruit "squashes" should be strained before use. Clear fruit cordials, for example, lime cordial, are generally suitable. In view of the desirability of avoiding drinks containing glucose, so as to reduce the risk of explosive concentrations of hydrogen or methane building up in the gut, "diet" drinks containing no or low sugar are especially suitable, for example liquid drinks for diabetics, diet Coke®, diet lemonade, dietary carbonated drinks or dietary cordials.

The time interval in the method of the invention is generally at least 4 hours, for example 6 hours or more, for example 8 hours or more. Typically, the time interval is less than 15 hours. The time interval between starting to take the first cleansing solution and starting to take the second cleansing solutions may be, for example, the time between an evening and the following morning, for example 12 to 16 hours, for example 14 hours. For example, the subject may sleep (for example overnight) between taking the first and second cleansing solutions. The time between finishing taking the first solution and starting to take the second solution is somewhat less, and that depends on the time the subject takes to complete the first solution. Typically, the first solution is taken over a period of up to two hours, for example an hour. Therefore the time between finishing taking the first solution and starting to take the second solution is for example 11 to 15 hours, for example 13 hours.

During the time interval between the administration of the first cleansing solution and the second cleansing solution, the subject may additionally take a stimulant laxative (also known as a prokinetic agent). A stimulant laxative can assist in bringing about good cleansing. Examples of stimulant laxatives include contact laxatives, for example bisacodyl, castor oil or senna. Examples of stimulant laxatives also include additional osmotic agents for example magnesium salts, for example magnesium citrate. If a stimulant laxatives is included in the regimen, the length of the time interval can be shortened. For example, it may be 1 to 15 hours, for example 1 to 12 hours, for example 2 to 10 hours.

During the time interval between the administration of the first cleansing solution and the second cleansing solution, it is very likely that the subject will experience a bowel movement. Advantageously, the subject waits until the bowel movement has occurred before taking the second cleansing solution.

The second cleansing solution, and optionally the first cleansing solution contains ascorbic acid, one or more salts thereof, or a mixture thereof. For convenience, they will be referred to herein as the "ascorbate component".

Suitable salts of the ascorbic acid include alkali metal and alkaline earth metal salts. For example, preferred salts of ascorbic acid include sodium ascorbate and magnesium ascorbate. In an embodiment, one of sodium ascorbate and magnesium ascorbate is present.

In one embodiment, the ascorbate component comprises both ascorbic acid and one or more salts of ascorbic acid. For example, the ascorbate component may comprise ascorbic acid and sodium ascorbate. For example, the ascorbate component may comprise ascorbic acid and magnesium ascorbate.

In an embodiment, a mixture of salts of ascorbic acid is used. For example, both sodium ascorbate and magnesium ascorbate may be present. They may be present with ascorbic acid, or without ascorbic acid.

The second cleansing solution contains a higher concentration of ascorbate anion than is present in the first cleansing solution. For example, the second cleansing solution contains twice the concentration of the ascorbate anion than the first cleansing solution or more. For example, the second solution contains three times or more, four times or more, or five times or more the concentration of the ascorbate anion than the first cleansing solution. For example, the second cleansing solution contains a concentration of the ascorbate anion that is at least 50 mmol per litre greater than that of the first cleansing solution. That is to say that the second solution contains a concentration of ascorbate anion that is at least 50 mmol per litre greater than that of the first solution. For example, the second solution contains a concentration of the ascorbate anion that is greater by at least 100 mmol per litre, for example at least 200 mmol per litre, at least 300 mmol per litre.

For example, the first cleansing solution may be substantially free from an ascorbate component.

For example, the second cleansing solution may comprise:
56.6 g sodium ascorbate, or
33.9 g sodium ascorbate and 20.1 g ascorbic acid, or
33.9 g sodium ascorbate, or
33.9 g sodium ascorbate and 21.4 g magnesium ascorbate.

The second cleansing solution may further comprise polyethylene glycol. The polyethylene glycol (PEG) may, for example, have an average molecular weight of 2500 to 4500 Da, for example 3000 to 4000 Da. For example, the PEG may be PEG 3350 or PEG 4000 as defined in national pharmacopeias. Further examples of suitable PEGs recognized in some national pharmacopeias include Macrogols, for example Macrogol 4000.

For example, the second cleansing solution may comprise 20 g or 40 g PEG 3350. For example, the second cleansing solution may have a volume of 500 ml.

The first cleansing solution may comprise polyethylene glycol and/or an alkali metal sulphate, an alkaline earth metal sulphate, or a mixture thereof.

The polyethylene glycol (PEG) in the first cleansing solution may be as described immediately above for the second cleansing solution. The PEG in the first cleansing solution can be a different PEG from the PEG in the second cleansing solution. For example, one PEG may be PEG3350 and the other PEG may be PEG4000. For example, the first cleansing solution may comprise 100 g PEG 3350. For example, the first cleansing solution may have a volume of 750 ml.

The first cleansing solution preferably comprises an alkali metal sulphate, an alkaline earth metal sulphate or a mixture thereof. An alkali metal or alkaline earth metal sulphate may, for example, be selected from sodium sulphate, potassium sulphate and magnesium sulphate. The solution may comprise more than one of sodium sulphate, potassium sulphate and magnesium sulphate, for example all three. Preferably, the alkali metal sulphate, an alkaline earth metal sulphate or the mixture thereof is or includes sodium sulphate. Preferably, an alkali metal sulphate or alkaline earth metal sulphate (for example sodium sulphate) is anhydrous.

For example, the first cleansing solution may have a volume of 750 ml and comprise 3 g, 6 g or 9 g of sodium sulphate.

The first and/or second cleansing solution(s) may further comprise one or more of:
a) one or more electrolytes;
b) one or more flavouring agents;
c) one or more sweeteners.

Electrolytes include salts of sodium, potassium, calcium and magnesium, particularly sodium and potassium; and salts of chloride, iodide, bicarbonate and carbonate, particularly chloride. Preferred electrolytes are sodium chloride and potassium chloride. In an embodiment, the first and/or second solution is substantially free from sodium bicarbonate.

For example, the first cleansing solution may have a volume of 750 ml and comprise 1.4 g sodium chloride and 0.3 g potassium chloride; or 1.6 g sodium chloride and 0.7 g potassium chloride; or 2.0 g sodium chloride and 1.0 g potassium chloride.

For example, the second cleansing solution may have a volume of 500 ml and comprise 3.5 g sodium chloride and 2.2 g potassium chloride; or 2.7 g sodium chloride and 1.3 g potassium chloride; or 2.8 g sodium chloride and 1.3 g potassium chloride; or 2.8 g sodium chloride and 2.0 g potassium chloride; or 3.1 g sodium chloride and 1.3 g potassium chloride. For example the second cleansing solution is substantially free from sodium bicarbonate.

In the solutions of the invention described herein, the quantities of the individual components recited do not include any solutes that may be present in the water used to prepare the solutions, for example, in hard water areas there may be significant amounts of $Ca^{2+}$ and $Mg^{2+}$ carbonates, bicarbonates or sulphates present in tap water.

The first and/or second cleansing solution(s) preferably include a flavouring agent. Flavouring for use in compositions of the invention should preferably mask saltiness, be relatively sweet but not excessively so, and be stable in the composition. Flavouring makes the solutions more palatable and thus aids patient compliance. Preferred flavourings include lemon e.g. Ungerer Lemon (available from Ungerer Limited, Sealand Road, Chester, England CH1 4LP) strawberry e.g. Ungerer Strawberry, grapefruit e.g. Ungerer Grapefruit flavouring powder, blackcurrant e.g. Ungerer Blackcurrant, pineapple e.g. IFF (International Flavours and Fragrances) Pineapple flavouring powder and vanilla/lemon and lime e.g. IFF Vanilla and Givaudin Roure Lemon and Lime Flav-o-lok. Those and further suitable flavourings are available from International Flavours and Fragrances Inc. (Duddery Hill, Haverhill, Suffolk, CB9 8LG, England), Ungerer & Company (Sealand Road, Chester, England CH1 4LP) or Firmenich (Firmenich UK Ltd., Hayes Road, Southall, Middlesex UB2 5NN). More preferred flavourings are lemon, kiwi, strawberry, grapefruit and orange. The most preferred flavourings are lemon flavour and orange flavour.

The first and/or second cleansing solution(s) preferably include a sweetener. Sugar-based sweeteners are generally not suited for colon cleansing compositions because the delivery of unabsorbed sugars to the colon provides a substrate for bacteria. Such sugars may be metabolised by the bacteria to form explosive gases such as hydrogen and methane. The presence of explosive gases in the colon can be highly dangerous when electrical apparatus is to be used during colonoscopy or other procedures. Preferred sweeteners include aspartame, acesulfame potassium (acesulfame K), sucralose and saccharine, and/or combinations thereof. For example, compositions of the invention may comprise one or both of aspartame and acesulfame potassium (acesulfame K). For example, compositions of the invention may comprise one or both of sucralose and acesulfame potassium (acesulfame K). Alternatively, compositions of the invention can be substantially free from added sweeteners, for example to minimize the number of different components in the compositions. Citric acid may also be present as a taste enhancer.

As mentioned above, in the various embodiments of the fourth aspect of the invention, the first or second solution may include electrolytes. In an alternative embodiment, some or all of the electrolytes may be provided in a tablet or capsule for co-administration with the respective solution. A tablet or capsule may include sweetener or flavouring.

The first cleansing solution may, for example, have a measured osmolality in the range 200 to 1500 mOsmol/kg. In a preferred embodiment, it is hyper-osmotic (that is to say that it has a higher osmotic strength than blood in the human body). It may, for example, have a measured osmolality in the range 320 to 1500 mOsmol/kg. For example, the measured osmolality of the first cleansing solution is in the range 330 to 1200 mOsmol/kg, for example 340 to 1000 mOsmol/kg, for example 350 to 800 mOsmol/kg, for example 350 to 700 mOsmol/kg.

The second cleansing solution is hyper-osmotic. That is to say that it has a higher osmotic strength than blood in the human body. It may, for example, have a measured osmolality in the range 500 to 2000 mOsmol/kg. For example, the osmolality may be in the range 700 to 1800 mOsmol/kg, for example 800 to 1700 mOsmol/kg, for example 900 to 1600 mOsmol/kg, for example 900 to 1300 mOsmol/kg, for example 1000 to 1300 mOsmol/kg.

In an embodiment, the second cleansing solution is more hyper-osmotic than the first cleansing solution. For example, the ratio between the osmolality of the second cleansing solution and the osmolality of the first cleansing solution is from 6:1 to 1.3:1. For example, the ratio is from 5:1 to 1.3:1, for example from 3.5:1 to 1.5:1, for example from 2.5:1 to 1.6:1.

Osmolality can be measured in various ways. In general, either freezing point depression or vapour-pressure alteration is used. For example, an Advanced Instruments, Inc Model 3250 osmometer (a freezing point depression device) can be used. Vapour pressure measurement can also be used, for example using an ELITech Group Vapro 5600 device. Osmolality values cited herein are preferably taken to be values measured using a freezing point depression osmometer, for example using an Advanced Instruments, Inc Model 3250 osmometer following standard operating procedure.

In general it is not necessary for the solutions to include preservatives or anti-oxidants. Nevertheless, low levels of anti-oxidants or preservatives may be used if required.

The method of the invention may be used to cleanse the colon prior to carrying out a diagnostic, therapeutic or surgical procedure on the colon, rectum or anus or elsewhere in the abdomen in a subject. The subject is most preferably a human. The diagnostic or surgical procedure may, for example, be colonoscopy, barium enema examination, sigmoidoscopy (for example flexible sigmoidoscopy) or colon surgery. The method of the invention may be a method of cleansing the colon prior to a surgical or diagnostic procedure comprising administering the first solution and then after a time interval administering the second solution prior to said procedure.

The solutions, compositions and kits described herein also find use in the treatment of constipation and faecal impaction. The invention thus provides solutions, compositions and kits as described herein for use in the treatment of constipation or faecal impaction. The invention also provides methods of treating constipation or faecal impaction comprising administration of solutions as described herein.

The invention further provides a kit comprising:
a first colon cleansing solution; and
a second colon cleansing solution, wherein the second colon cleansing solution is hyper-osmotic and contains ascorbic acid, one or more salts of ascorbic acid, or a mixture thereof; and wherein the first colon cleansing solution is either substantially free from ascorbic acid and salts thereof, or contains ascorbic acid, one or more salts of ascorbic acid, or a mixture thereof, in an amount providing a lower concentration of ascorbate anion in the first colon solution than is present in the second colon cleansing solution.

A kit may further comprise instructions for use. The use may be as described above in relation to methods of the invention.

In a kit of the invention, the components of the first and second solutions are as described hereinabove in relation to the methods of the invention.

The invention further provides a first solution, and a second solution, for use in a method of cleansing the colon of a subject comprising:
the subject taking an effective amount of a first cleansing solution; and then after a time interval
the subject taking an effective amount of a second cleansing solution,
wherein the second cleansing solution is hyper-osmotic and contains ascorbic acid, one or more salts of ascorbic acid, or a mixture thereof; and wherein the first cleansing solution is either substantially free from ascorbic acid and salts thereof, or contains ascorbic acid, one or more salts of ascorbic acid, or a mixture thereof, in an amount providing a lower concentration of ascorbate anion than is present in the second cleansing solution.

The invention further provides a solution that is hyper-osmotic and contains ascorbic acid, one or more salts of ascorbic acid, or a mixture thereof, for use in a method of cleansing the colon of a subject comprising:
the subject taking an effective amount of a first cleansing solution; and then after a time interval
the subject taking an effective amount of a second cleansing solution,
wherein the second cleansing solution is hyper-osmotic and contains ascorbic acid, one or more salts of ascorbic acid, or a mixture thereof; and wherein the first cleansing solution is either substantially free from ascorbic acid and salts thereof, or contains ascorbic acid, one or more salts of ascorbic acid, or a mixture thereof, in an amount providing a lower concentration of ascorbate anion than is present in the second cleansing solution.

The solutions for use in a method of cleansing the colon in accordance with the invention are as described hereinabove in relation to the methods of the invention.

In an embodiment, the invention provides a kit comprising:
a) a first component, being a composition for the preparation of a first colon cleansing solution by admixture with a clear fluid (for example water); and
b) a second component, being a composition for the preparation of a second colon cleansing solution by admixture with a clear fluid (for example water),
and instructions for use that specify the volume to which each component is to be made up with water,
wherein the second colon cleansing solution, when made up to the instructed specified volume with the clear fluid (for example water), is hyper-osmotic and contains ascorbic acid, one or more salts of ascorbic acid, or a mixture thereof; and wherein the first colon cleansing solution is either substantially free from ascorbic acid and salts thereof, or contains, when made up to the instructed specified volume with the clear fluid (for example water), ascorbic acid, one or more salts of ascorbic acid, or a mixture thereof, in an amount providing a lower concentration of ascorbate anion in the first colon solution than in the second colon cleansing solution.

The constituent parts of the composition for the preparation of a first cleansing solution by admixture with water are, for example, as described hereinabove in relation to the first solution in the methods of the invention. The constituent parts of the composition for the preparation of a second cleansing solution by admixture with water are, for example, as described hereinabove in relation to the second solution in the methods of the invention.

For example, components a) and b) may be in dry powder, granular or other dry form. They may alternatively be in the form of concentrates or slurries. Components a) and b) may be in the same or different physical forms. Components within a) and b) may be in the same or different physical forms. For example, one or both of components a) and b) are dry powders.

In an embodiment, a kit of the invention has instructions in which the specified volume of water for each solution is less than one litre. For example, the combination of the specified volumes of the first and second cleansing solutions is preferably less than 2 litres. Preferably, it is 1750 ml or less, for example 1500 ml or less, for example 1250 ml or less. For most adult subjects, a combined volume of more than 500 ml is used, for example more than 750 ml. For example, a combined volume of from 500 ml to 1750 ml is used, for example from 750 ml to 1500 ml, for example from 1000 ml to 1500 ml, for example 1250 ml. For example a volume of 750 ml may be specified for the first cleansing solution and a volume of 500 ml may be specified for the second cleansing solution. The instructions may specify that a cleansing solution is consumed immediately after it has been prepared. They may specify that the cleansing solution is prepared and then stored in a fridge before consumption at a slightly later time.

In general, the instructions specify that the first and second solutions are to be ingested in succession with a time interval between them. In an embodiment, the instructions specify that the first cleansing solution is ingested first followed, after a time interval (for example the time between an evening and the following morning) by ingestion of the second cleansing solution. The time interval is preferably as described above in relation to the methods of the invention.

It is convenient for the patient for a kit of the invention to be provided in the form of, for example, a box. In a kit of the invention the first and/or second components may each be contained in one or more containers. In particular, the second component may be contained in more than one container. For example, if the second component comprises both ascorbic acid and PEG then the ascorbic acid and PEG may be contained in separate containers. The other constituents of the second component (for example one or more of sodium chloride, potassium chloride and sodium sulphate) may be in either of the separate containers. For example, they may be in the container containing the PEG.

If a flavouring component and/or sweetening component is present in the first or second solution, then in a kit of the invention, the flavouring and/or sweetener component for the relevant solution may be provided in a separate container from the other constituents of that solution. Alternatively, the flavouring and/or sweetener may be in the same container as one or more other components. For example, any flavouring or sweetener may be in the same container as PEG.

Examples of suitable containers include tubs, bags and sachets. A preferred container is a sachet.

In one embodiment, a kit comprises:
a) a first sachet comprising a first composition for the preparation of a first cleansing solution;
b) a second sachet;
c) a third sachet;
and instructions for use
wherein the second and third sachets together provide a composition for the preparation of a second colon cleansing solution, and
wherein the first and second cleansing solutions are as described herein-above.

For example, in a kit of the invention as mentioned immediately above:
a) the first sachet comprises polyethylene glycol and/or sodium sulphate, optional flavouring and/or optional sweetener;
b) the second sachet comprises polyethylene glycol, and optionally further components including one or more selected from an alkali metal sulphate, an alkaline earth metal sulphate, or a mixture thereof, electrolytes, one or more salts of ascorbic acid, flavouring and sweetener; and
c) the third sachet comprises ascorbic acid and optionally one or more salts of ascorbic acid.

A kit may contain one treatment, for example a cleansing treatment, or several treatments. A treatment generally comprises one dose of the first cleansing solution and one dose of the second cleansing solution. In a kit of the invention, preferably the first component comprises one dose of the first cleansing solution, and the second component comprises one dose of the second cleansing solution.

For example, in a kit of the invention:
a) the first sachet comprises 100 g PEG 3350, 3 g sodium sulphate, 1.4 g sodium chloride and 0.3 g potassium chloride; or 100 g PEG 3350, 6 g sodium sulphate, 1.6 g sodium chloride and 0.7 g potassium chloride; or 100 g PEG 3350, 9 g sodium sulphate, 2.0 g sodium chloride and 1.0 g potassium chloride; and optional flavouring and/or optional sweetener;
b) the second sachet comprises (i) 40 g PEG 3350, 3.5 g sodium chloride and 2.2 g potassium chloride; or (ii) 20 g PEG 3350 2.7 g sodium chloride and 1.3 g potassium chloride; or (iii) 40 g PEG 3350, 2.8 g sodium chloride and 1.3 g potassium chloride; or (iv) 40 g PEG 3350, 2.8 g sodium chloride and 2.0 g potassium chloride; or (v) 40 g PEG 3350, 3.1 g sodium chloride and 1.3 g potassium chloride; and optional flavouring and/or optional sweetener; and
c) the third sachet comprises for use with the respectively numbered second sachet (i) 56.6 g sodium ascorbate; or (ii) and (iii) 33.9 g sodium ascorbate and 20.1 g ascorbic acid; or (iv) 33.9 g sodium ascorbate; or (v) 33.9 g sodium ascorbate and 21.4 g magnesium ascorbate.

In such kits, the contents of the sachets may consist essentially of the recited components.

As mentioned above, some or all of the electrolytes may be provided in a tablet or capsule for co-administration with the respective solution. Accordingly, in a kit as described immediately above, some or all of the sodium chloride and potassium chloride in the first or second sachet may instead be provided in a tablet or capsule.

In an embodiment, the kit can be provided to the subject with a plurality of flavouring agents (each optionally with one or more sweeteners), each separately packaged. The subject can then select a preferred flavouring (or flavouring and sweetener combination) according to his or her taste. The subject also has the choice of not using any flavouring or sweetener at all.

Unless stated otherwise, a composition that is described herein as comprising a recited set of components is to be taken as comprising the components in admixture. If a composition is said to be presented in two or more parts, then the components need not all be in physical admixture. Typically, they are provided together in the article provided to the subject.

To summarise, the invention provides a colon cleansing solution comprising (or consisting essentially of):
a) 300 to 2000 mmol per litre ascorbate anion (provided by ascorbic acid, one or more salts of ascorbic acid selected from sodium ascorbate, potassium ascorbate, magnesium ascorbate and calcium ascorbate, or a mixture thereof); preferably 350 to 800 mmol;
b) 10 to 200 g per litre PEG having an average molecular weight of 3000 to 4000 Da; preferably 20 to 100 g per litre
c) optionally sodium chloride (for example 3 to 7 g per litre) and potassium chloride (for example 2 to 5 g per litre);
d) optionally sodium sulphate (if present, for example 2 to 20 g per litre);
e) optionally one or more flavouring agents; and
f) optionally one or more sweeteners.

The invention also provides a composition (optionally presented in two or more parts) for admixture with water to provide a solution of the invention. The electrolytes may optionally be provided as a tablet or a capsule to be co-administered with the solution.

The invention also provides a method of cleansing the colon of a subject comprising:
administering to the subject an effective amount of a first cleansing solution; and then after a time interval
administering to the subject an effective amount of a second cleansing solution,
wherein the second cleansing solution is hyper-osmotic and contains ascorbic acid, one or more salts of ascorbic acid, or a mixture thereof (for example ascorbic acid and sodium ascorbate, for example sodium ascorbate); and wherein the first cleansing solution is either substantially free from ascorbic acid and salts thereof, or contains ascorbic acid, one or more salts of ascorbic acid, or a mixture thereof, in an amount providing a lower concentration of ascorbate anion than is present in the second cleansing solution. The second cleansing solution may comprise PEG and electrolytes (for example sodium chloride and potassium chloride). The first solution may comprise PEG; it may comprise an alkali metal or alkaline earth metal sulphate (for example sodium sulphate); it may comprise electrolytes (for example sodium chloride and potassium chloride). There are also provided kits comprising a first and a second solution according to the invention, and kits comprising compositions for preparing the first and second solutions.

EXPERIMENTAL

Pharmacokinetic Evaluation and Mass Balance Study

Figure 1:
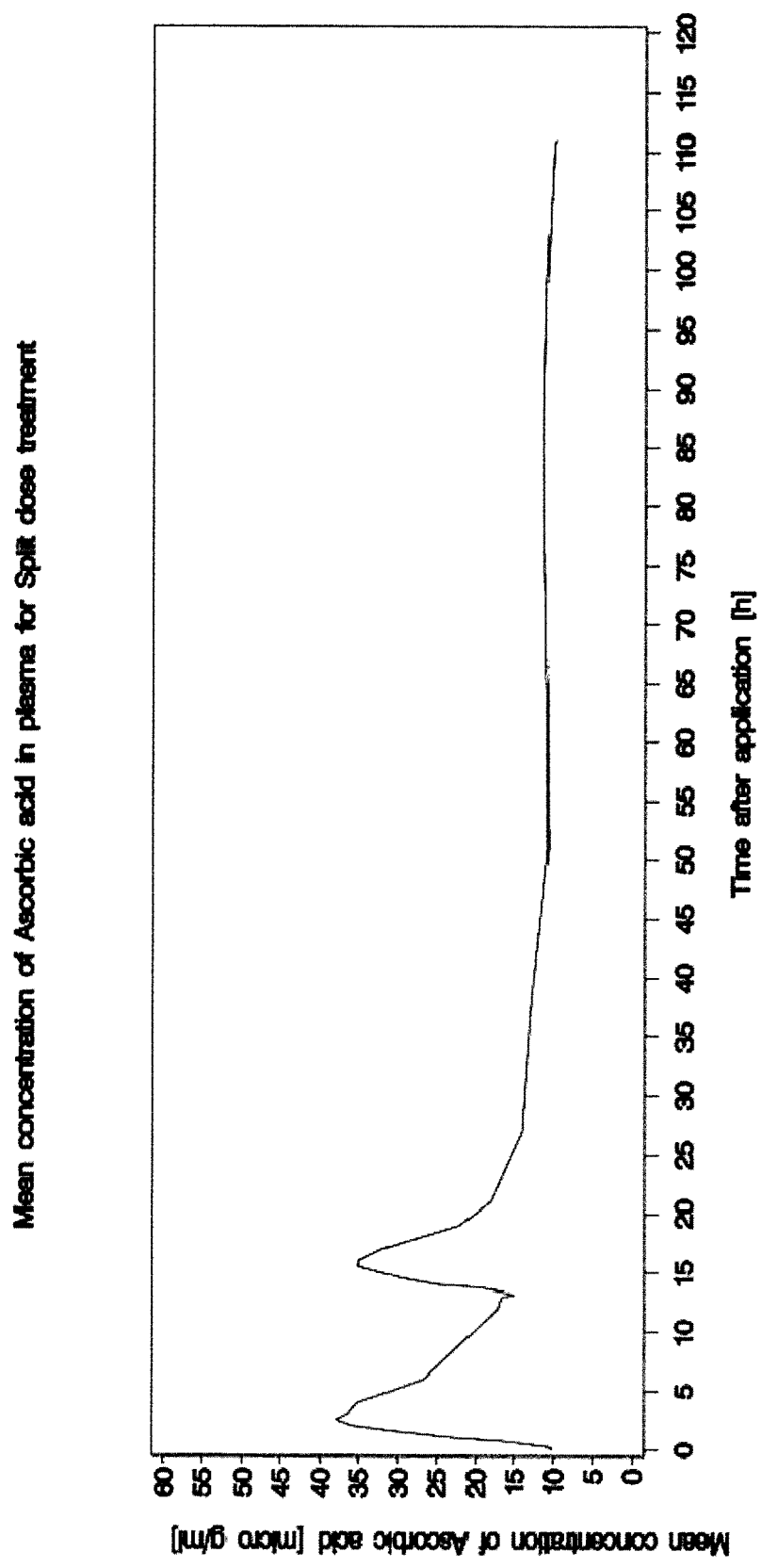
FIG. 1 is a graph showing the mean concentration of ascorbic acid (µg/ml) in plasma over time in subjects receiving the split dose treatment of MOVIPREP.

An investigation into the pharmacokinetics and mass balance of a solution in water of MOVIPREP powder for oral solution was carried out following oral administration using single dose or split dose intake in healthy male subjects.

Subjects:

The subjects were healthy male volunteers aged 18 to 45 years. The subjects' written informed consent was obtained. The subjects were willing, able and competent to complete the procedure and to comply with the study instructions. The subjects had to not meet any of the exclusion criteria. 24 subjects were randomly allocated into two groups: 12 into the single-dose group and 12 into the split-dose group.

Study Medication:

The study medication administered was a solution in water of MOVIPREP powder for oral solution. The total dose was 2 litres of the solution for each subject. The solution contains, per litre:

PEG3350: 100 g
Sodium Sulphate: 7.500 g
Ascorbic Acid: 4.700 g
Sodium Ascorbate: 5.900 g
Sodium chloride: 2.691 g
Potassium chloride: 1.015 g
Lemon-flavour and Sweetener The 4.700 g ascorbic acid and 5.900 g sodium ascorbate together provide the equivalent of 9.944 g ascorbic acid. A 2 litre dose thus provides the equivalent of 19.89 g of ascorbic acid.

Treatment Regimens:

The single dose group took the solution as follows:

2 L of solution were consumed between 17:00 and 20:00 on Day −1. The first litre was consumed within the first hour, with at least 500 ml of additional clear fluid. The second litre was consumed within two hours, with at least 500 ml of additional clear fluid.

The split dose group took the solution as follows:

1 L of solution was consumed between 18:00 and 19:30 on Day −1. The litre was consumed within the 90 minutes, with at least 500 ml of additional clear fluid. The second litre was consumed between 07:00 and 08:30 on Day 0 (the day on which a colonoscopy procedure would be carried out in a clinical situation). The litre was consumed within the 90 minutes, with at least 500 ml of additional clear fluid.

Sample collection for monitoring of PK parameters in blood and recovery of components in faeces and urine:

Urine and faeces were collected throughout the procedure. Cumulative content amounts of components under investigation in the urine were obtained from measured concentrations of the components and measured actual volume of urine. Similarly, the cumulative content amounts of components under investigation in the faeces were obtained from measured concentrations of the components and measured actual mass of faeces. The defined time points for analysis of urine and faeces were at 0 hr, 2 hr, 4 hr, 8 hr, 12 hr, 12.97 hr, 18 hr, 24 hr, 25.93 hr, 36 hr, 48 hr, 60 hr, 72 hr and 120 hr after the start of intake of the first litre of study medication. Blood samples were collected from the subjects at particular time points through the procedure.

Sample Evaluation:

The cumulative amounts of ascorbic acid, PEG3350, chloride, sulphate, sodium and potassium in plasma, faeces and urine were evaluated. The PK profiles of ascorbic acid, PEG3350, chloride, sulphate, sodium and potassium in the plasma were evaluated. Plasma renin and aldosterone were checked at all PK time points.

For higher accuracy, the analysis of the recovery of ascorbic acid was extended to include also its metabolites dehydro-ascorbic acid and oxalic acid in urine and faeces.

Completion of Study:

Of the 12 subjects in the single-dose group, 4 had to be excluded from the analysis due to protocol violations, so 8 subjects were evaluated.

Of the 12 subjects in the split-dose group, 1 had to be excluded from the analysis due to protocol violations, so 11 subjects were evaluated.

Results:

General:

The mean cumulative recovery of ascorbic acid (including metabolites dehydroascorbic acid and oxalic acid) and PEG3350 in faeces and urine was comparable for the subjects in both treatment groups. The data collected on the cumulative amount of chloride, sulphate, sodium and potassium were comparable between the subjects in both treatment groups insofar as there was a continuous elimination in urine plus faeces (i.e. no plateau was reached). Furthermore, the PK parameters ($AUC_{0-\infty}$, $AUC_{last}$, $C_{max}$, $K_{el}$, $V_d$ and $t_{1/2}$) determined for ascorbic acid, sulphate, chloride, sulphate, sodium and potassium were comparable for the subjects in the single dose and the split dose group; especially the values for $AUC_{last}$ (i.e. exposure) were nearly identical for both groups.

Figure 2:
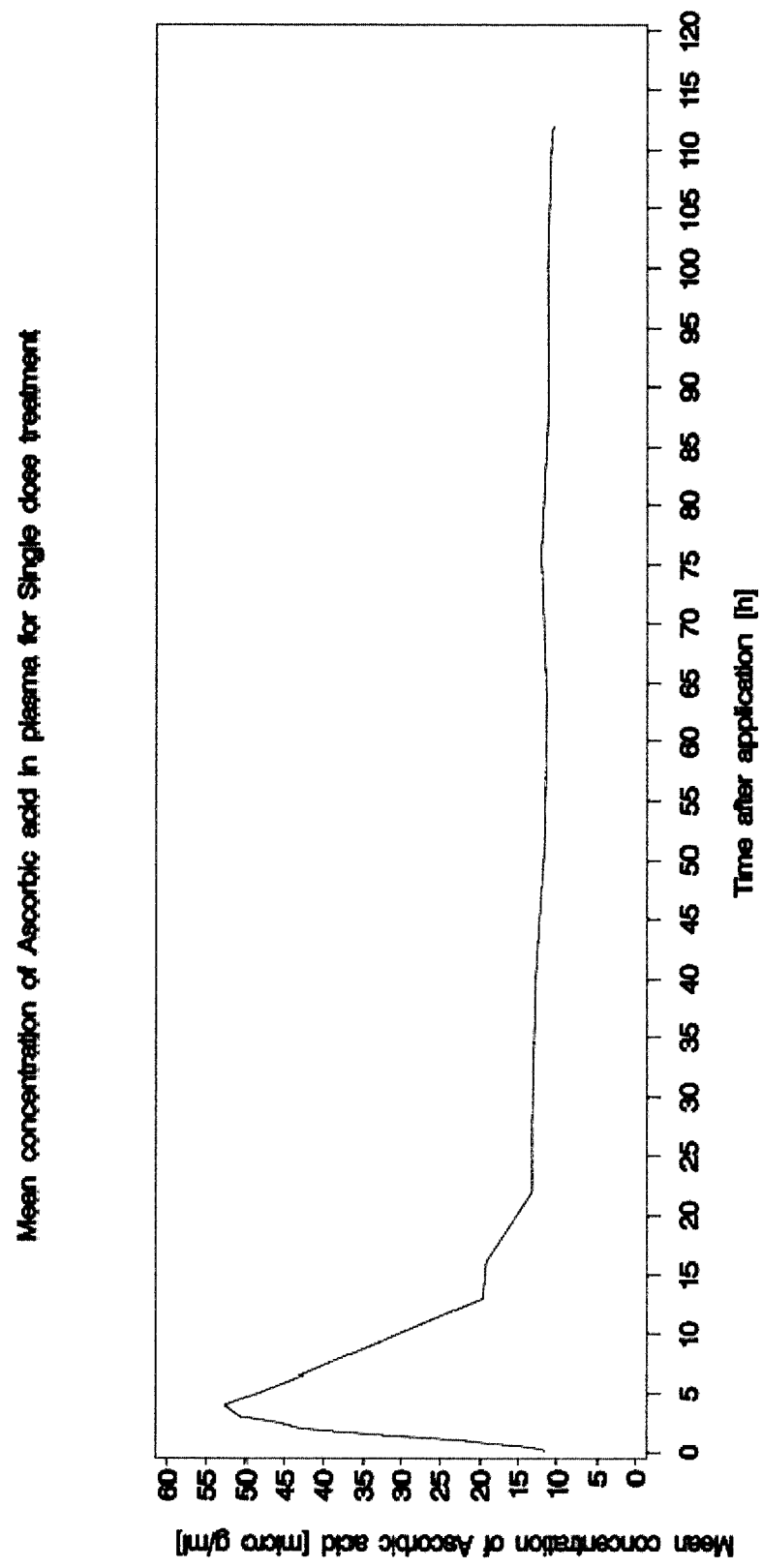
FIG. 2 is a graph showing the mean concentration of ascorbic acid (µg/ml) in plasma over time in subjects receiving the single dose treatment of MOVIPREP.

Recovery and Mass Balance of Ascorbic Acid:

The ascorbic acid was to a significant extent excreted in faeces. The cumulative recovery of ascorbic acid and its metabolites from 0 to 120 hours after the start of intake of the first litre of study medication is shown in Table 1 for the single-does group and in Table 2 for the split-dose group. In the final column of Tables 1 and 2, there is given the plasma concentration of ascorbate (not including its metabolites) at the stated time points. That information in Tables 1 and 2 is taken from the graphs shown in FIGS. 1 and 2 respectively.

TABLE 1

| | Single Dose Group | | | |
|---|---|---|---|---|
| Time/hr | Urine/g | Faeces/g | Total/g | Plasma µg/ml |
| 0 | 0.000 ± 0.000 | 0.000 ± 0.000 | 0.00 ± 0.000 | 11.5 |
| 2 | 0.125 ± 0.0964 | 4.718 ± 3.5639 | 4.84 ± 3.643 | 43.0 |
| 4 | 0.456 ± 0.1193 | 11.961 ± 1.4291 | 12.42 ± 1.418 | 52.5 |
| 8 | 1.278 ± 0.2492 | 13.577 ± 1.2776 | 14.86 ± 1.243 | 38.0 |
| 12 | 1.472 ± 0.3116 | 13.587 ± 1.2882 | 15.06 ± 1.248 | 23.0 |
| 12.97 | 1.472 ± 0.3116 | 13.587 ± 1.2882 | 15.06 ± 1.248 | 20.0 |
| 18 | 2.202 ± 0.4252 | 13.909 ± 1.2864 | 16.11 ± 1.253 | 17.2 |
| 24 | 2.740 ± 0.5025 | 13.947 ± 1.2870 | 16.69 ± 1.210 | 13.2 |
| 25.93 | 2.814 ± 0.5112 | 13.952 ± 1.2859 | 16.77 ± 1.218 | 13.2 |
| 36 | 3.162 ± 0.6042 | 13.952 ± 1.2860 | 17.11 ± 1.209 | 12.8 |
| 48 | 3.977 ± 0.7192 | 13.972 ± 1.2901 | 17.95 ± 1.369 | 12.3 |
| 60 | 4.605 ± 0.9177 | 13.982 ± 1.2964 | 18.59 ± 1.733 | 12.0 |
| 72 | 5.104 ± 1.1514 | 14.018 ± 1.3020 | 19.12 ± 1.920 | 12.3 |
| 120 | 6.501 ± 1.9053 | 14.041 ± 1.3203 | 20.54 ± 2.723 | Not measured |
| From 12.97 to 25.93 | 1.342 ± 0.4857 | 0.365 ± 0.4459 | 1.707 ± 0.780 | N/A |

TABLE 2

Split Dose Group

| Time/hr | Urine/g | Faeces/g | Total/g | Blood μg/ml |
|---|---|---|---|---|
| 0 | 0.000 ± 0.000 | 0.000 ± 0.000 | 0.00 ± 0.000 | 10.5 |
| 2 | 0.248 ± 0.3552 | 2.356 ± 2.0088 | 2.60 ± 2.213 | 36.5 |
| 4 | 0.586 ± 0.3951 | 3.810 ± 2.4661 | 4.40 ± 2.592 | 34.3 |
| 8 | 0.860 ± 0.5437 | 4.836 ± 2.4106 | 5.70 ± 2.607 | 25.0 |
| 12 | 0.860 ± 0.5437 | 4.836 ± 2.4106 | 5.70 ± 2.607 | 16.2 |
| 12.97 | 1.180 ± 0.6712 | 5.022 ± 2.4831 | 6.20 ± 2.772 | 15.0 |
| 18 | 2.220 ± 0.7555 | 10.239 ± 4.6259 | 12.46 ± 4.885 | 25.5 |
| 24 | 3.323 ± 1.3183 | 11.010 ± 4.5147 | 14.33 ± 4.993 | 16.0 |
| 25.93 | 3.482 ± 1.3946 | 11.047 ± 4.5342 | 14.53 ± 5.123 | 15.8 |
| 36 | 4.351 ± 2.3023 | 11.062 ± 4.5147 | 15.41 ± 5.556 | 13.0 |
| 48 | 5.432 ± 3.3304 | 11.104 ± 4.5497 | 16.54 ± 6.200 | 11.6 |
| 60 | 6.228 ± 3.9837 | 11.109 ± 4.5519 | 17.34 ± 6.685 | 11.4 |
| 72 | 7.069 ± 4.5654 | 11.141 ± 4.5649 | 18.21 ± 7.104 | 11.4 |
| 120 | 9.123 ± 5.4605 | 11.195 ± 4.6225 | 20.32 ± 7.930 | Not measured |
| From 12.97 to 25.93 | 2.302 ± 1.2932 | 6.025 ± 2.4704 | 8.327 ± 3.113 | N/A |

Discussion:

Of the 19.89 g ingested ascorbic acid equivalents contained in 2 litres of MOVIPREP solution 103.35% were found to be recovered in urine and faeces of the single-dose group subjects after 120 hours, and 103.05% were found to be recovered in urine and faeces of the subjects in the split-dose group after 120 hours. There was no statistically significant difference between the total recovered amount of ascorbic acid between the two groups.

There was, however, a difference between the timing of the recovery and between the distribution of the ascorbic acid between urine and faeces. It is seen in Tables 1 and 2 that in the split dose group, the distribution of the total recovered 20.32 g ascorbic acid between urine and faeces is in the ratio 9.123 g:11.195 g, ie 44.9%:55.1% (or 1:1.23) whilst, in the single dose group, the distribution of the total recovered 20.54 g ascorbic acid between urine and faeces is in the ratio 6.501 g:14.041 g, ie 31.6%:68.4% (or 1:2.16).

The final column of each of Tables 1 and 2 shows the plasma level of ascorbate/ascorbic acid at the stated time points. The measurement does not include metabolites of ascorbic acid, and it does not take account of ascorbate in other compartments in the body. Nevertheless, increases in plasma ascorbate are clearly seen in the hours following administration of the solution.

In order to compare the recovery of ascorbic acid during the different phases of the protocol, two time intervals were defined: the first time interval was between time zero, i.e. the start of the intake of the first litre of study medication and time "x", where "x" represents the minimal starting time point of the intake of the second litre of study medication for split dose group (from time 0 to 12.97 hrs). The second time interval was from time "x" to time 2× (from 12.97 to 25.93 hrs).

It is seen that, during the second time interval, 6.025 g of ascorbic acid are recovered from faeces of the split-dose group, compared with 5.022 g during the first time interval. The 6.025 g in the second time interval is closer to being half of the 13.587 g seen over the first time interval in the single-dose group. That is to say that the second dose of the split-dose treatment follows a similar time course to the (only) dose in the single-dose treatment.

The differences in the recovered amounts of components between the first and the second time intervals are statistically significant for ascorbic acid (incl metabolites) in faeces ($p=0.0078$) and urine plus faeces ($p=0.0078$) for the single dose group subjects, and in urine ($p=0.0020$) and urine plus faeces ($p=0.0322$) of the split dose group subjects.

EXAMPLES

1. Bowel Cleansing Solutions

Example 1a—Contents of Solutions

The following bowel cleansing solutions of the invention were prepared. For solution A1, the components shown in Table 3 were combined in dry powder form and sealed in a sachet. The solution was then prepared by dissolving the contents in water to the volume stated in the penultimate column. Solutions A2 and A3 were prepared in an analogous manner.

TABLE 3

| Sol'n | PEG3350/ g | Na$_2$SO$_4$ (anhyd)/g | NaCl/g | KCl/g | Water to Vol/ml | V (350)/ ml |
|---|---|---|---|---|---|---|
| A1 | 100 | 3 | 1.4 | 0.3 | 750 | 725 |
| A2 | 100 | 6 | 1.6 | 0.7 | 750 | 915 |
| A3 | 100 | 9 | 2.0 | 1.0 | 750 | 1080 |

For solution B1, the components shown in Table 4 were combined in dry powder form and sealed in respective sachets A and B as indicated in the table. The solution was then prepared by mixing the contents of the two sachets together and then dissolving them in water to the volume stated in the penultimate column. Solutions B2 to B5 were prepared in an analogous manner.

TABLE 4

| | Sachet A | | | | Sachet B | | | Water | |
|---|---|---|---|---|---|---|---|---|---|
| Sol'n | PEG3350/g | Na$_2$SO$_4$ (anhyd)/g | NaCl/g | KCl/g | Sodium Ascorbate/g | Ascorbic Acid/g | Magnesium Ascorbate/g | to Vol/ ml | V (350)/ ml |
| B1 | 40 | — | 3.5 | 2.2 | 56.6 | — | — | 500 | 2000 |
| B2 | 20 | — | 2.7 | 1.3 | 33.9 | 20.1 | — | 500 | 1570 |
| B3 | 40 | — | 2.8 | 1.3 | 33.9 | 20.1 | — | 500 | 1600 |
| B4 | 40 | 6 | 2.8 | 2.0 | 33.9 | — | — | 500 | 1700 |
| B5 | 40 | — | 3.1 | 1.3 | 33.9 | — | 21.4 | 500 | 1700 |

The solutions additionally contained sweetener and flavouring sufficient to improve their palatability.

In the case of the solutions in Table 4, those components were in sachet A. The solutions were not optimised for palatability.

Example 1b—V(350) Osmolality Measurements

In order to assess the osmotic strength of the solutions, it was determined how much water was required to provide a solution with measured osmolality of 350 mOsmol/kg from the amounts of the components in Tables 3 and 4.

To each solution prepared by dissolving the components in Tables 3 and 4 above in 500 ml of deionised was added further deionised water until it reached an osmolality of 350 mOsmol/kg. After a volume was found in a first experiment, a second experiment was carried out in which the volume of water found in the first experiment was added to the contents of a new sachet in one aliquot. It was then checked that the resulting solution had an osmolality of 350+/−7 mOsmol/kg. In every case, it did. The volumes are recorded in Tables 3 and 4 in the final columns Osmolalities were measured using an Advanced Instruments, Inc Model 3250 osmometer. The osmometer was operated following standard instructions: after the device passes a calibration check, the "Low Range" osmolality range (0 to 2000 mOsmol/kg) is selected, and a sample tube containing 250 μl of sample solution is placed in the freezing chamber. The "start" button is then pressed. When the measurement is completed, the device displays the measurement result and that is recorded.

Example 2: Bowel Cleansing of Subjects

An open, randomised, single centre phase I study to investigate the pharmacodynamic effects (stool weight) of the various modified gut cleansing solutions. The study had two sequential parts (Part 1 and Part 2). In both parts investigational medicinal product (IMP) was administered in the evening of Day 1 and the morning of Day 2. In Part 1 of the study, three different solutions A given in the evening were combined in turn with a fixed solution B given in the morning. In addition, one group of subjects received MOVIPREP®, as reference product.

In Part 2 of the study, the selected solution A from Part 1 was given as the evening dose in combination with four different solutions B as the morning dose. Stool output was assessed.

Number of Patients (Planned and Analysed):
Planned: at least 160 evaluable cases in the entire study (20 evaluable subjects per treatment group)
Analysed: 161 evaluable cases (part A: 81 subjects; part B: 80 subjects). Patients were subjected to inclusion and exclusion criteria.

Dosage Regimen:
Each subject received his/her solution regimen in the split dose intake:
Evening dose: Day 1; start intake between 17:00 and 18:00 pm for an intake period of up to 2 hours after fasting from 14:00 pm.
Morning dose: Day 2; start intake between 7:00 and 8:00 am for an intake period of up to 2 hours. 4 hours after complete intake of the morning dose, the first meal was provided, but not before completion of the planned safety laboratory blood drawing.

After the end of the intake of each dose of the investigational solution, the subjects were instructed to take further clear liquid (water).

Screened healthy subjects provided one stool collection after a complete bowel motion in the 7 days before the planned admission to the unit for baseline evaluation. After admission to the unit, all defecated faeces were collected after each bowel movement. Stool appearance and weight was determined for each collected stool fraction. Faecal samples were taken until at least 15:00 pm on Day 4 and an attempt was made to collect a final faecal sample prior to discharge from the phase I unit.

Solutions: Part 1:

TABLE 5a

| Sol'n | PEG3350/g | $Na_2SO_4$ (anhyd)/g | NaCl/g | KCl/g | Ascorbic acid | Sodium ascorbate | Water to Vol/ml |
|---|---|---|---|---|---|---|---|
| A2 | 100 | 6 | 1.6 | 0.7 | — | — | 750 |
| A3 | 100 | 9 | 2.0 | 1.0 | — | — | 750 |
| A4 | 75 | 5.6 | 2.0 | 0.8 | — | — | 750 |
| A-Mov | 100 | 7.5 | 2.691 | 1.015 | 4.7 | 5.9 | 1000 |

TABLE 5b

| | Sachet A | | | | Sachet B | | | Water |
|---|---|---|---|---|---|---|---|---|
| Sol'n | PEG3350/g | $Na_2SO_4$ (anhyd)/g | NaCl/g | KCl/g | Sodium Ascorbate/g | Ascorbic Acid/g | Magnesium Ascorbate/g | to Vol/ml |
| B3 | 40 | — | 2.8 | 1.3 | 33.9 | 20.1 | — | 500 |
| B-Mov | 100 | 7.5 | 2.691 | 1.015 | 5.9 | 4.7 | — | 1000 |

The subjects were randomised into four groups (1:1:1:1), and given one of the three solutions A2, A3 and A4 in Table 5a as the evening dose, followed by solution B3 as the morning dose, or (for the fourth group) given MOVIPREP solution for both doses (ie A-Mov followed by B-Mov). Solutions A2 and A3 are solutions of the invention. Solution A4 is a reference solution. Solutions A-Mov and B-Mov are the commercially available MOVIPREP solution. Each of solutions A2 to A4 was taken in a dose of 750 ml; the MOVIPREP solution was taken in a dose of 1000 ml as indicated in the product instructions.

In addition to the investigation formulations intake, the subjects were instructed to take further clear liquid (water). In the case of solutions A2 to A4, they were instructed to take 1750 mL of further clear liquid (875 mL after the evening dose, and 875 mL after the morning dose). In the case of A-Mov, MOVIPREP®, they were instructed to take 1000 mL of further clear liquid (500 mL after the evening dose, and 500 mL after the morning dose).

Solutions: Part 2:

TABLE 6a

| Sol'n | PEG3350/g | $Na_2SO_4$ (anhyd)/g | NaCl/g | KCl/g | Ascorbic acid | Sodium ascorbate | Water to Vol/ml |
|---|---|---|---|---|---|---|---|
| A3 | 100 | 9 | 2.0 | 1.0 | — | — | 750 |

TABLE 6b

| | Sachet A | | | | | Sachet B | | | Water |
|---|---|---|---|---|---|---|---|---|---|
| Sol'n | PEG3350/g | $Na_2SO_4$ (anhyd)/g | NaCl/g | KCl/g | $NaHCO_3$/g | Sodium Ascorbate/g | Ascorbic Acid/g | Magnesium Ascorbate/g | to Vol/ml |
| B1 | 40 | — | 3.5 | 2.2 | — | 56.6 | — | — | 500 |
| B4 | 40 | 6 | 2.8 | 2.0 | — | 33.9 | — | — | 500 |
| B5 | 40 | — | 3.1 | 1.3 | — | 33.9 | — | 21.4 | 500 |
| B6 | 29 | 4.8 | 1.4 | 0.9 | 2.2 | — | 23.3 | — | 500 |

The subjects were randomised into four groups (1:1:1:1), and given solution A3 in Table 6a as the evening dose, followed by one of solutions B1, B4, B5 and B6 as the morning dose. Solutions B1, B4 and B5 are solutions of the invention. Solution B6 is a reference solution.

In addition to the investigation formulations intake, the subjects were instructed to take further clear liquid (water). In each case, they were instructed to take 1750 mL of further clear liquid (875 mL after the evening dose, and 875 mL after the morning dose).

Efficacy:

The primary variable in the clinical study was the stool weight output generated by the investigational solutions (combined evening and morning dosing on Day 1 and Day 2) over 24 hours from the start of the intake of the evening solution. The reference value of the study was set to a stool weight of approximately 2500 g or greater, which it is desired to be reached in order to demonstrate positive pharmacodynamic effects indicating a potential as a colon cleansing agent.

In addition to the primary trial variable mentioned above, stool output was separately measured and recorded for a) the time between when the subject starts to take the evening dose (17:00 to 18:00 on Day 1) and the time the subject starts to take the morning dose (7 am to 8 am on Day 2); and b) the time the subject starts to take the morning dose (7 am to 8 am on Day 2) and midnight on Day 2.

Results:

TABLE 7a

Study Part 1: Stool Weight (g); full analysis set (FAS, N = 81)

| Treatment | N | 24 hr Median/g | 24 hr Mean/g | 24 hr STD/g |
|---|---|---|---|---|
| A2 + B3 | 20 | 2981.3 | 3021.2 | 599.5 |
| A3 + B3 | 21 | 3493.2 | 3386.1 | 602.74 |
| A4 + B3 | 20 | 2796.80 | 2794 | 688.27 |
| A-Mov + B-Mov | 20 | 3145.95 | 2973.7 | 479.41 |

In the table, the "24 hr Median" is the median stool output in the 24 hours from the time the subject starts to take the evening dose (ie 17:00 to 18:00 on Day 1 to the same time on Day 2); the "24 hr Mean" is the mean of the 24 hour data, and the STD is the standard deviation.

TABLE 7b

Study Part 1: Stool Weight (g); full analysis set (FAS, N = 81)

| Treatment | N | pm stool median/g | am stool median/g | pm stool mean/g | am stool mean/g |
|---|---|---|---|---|---|
| A2 + B3 | 20 | 925.8 | 2380.0 | 867.07 | 2196.9 |
| A3 + B3 | 21 | 1178.5 | 2405.7 | 1184.34 | 2262.39 |
| A4 + B3 | 20 | 826.7 | 2244.8 | 832.33 | 2005.25 |
| A-Mov + B-Mov | 20 | 1629.2 | 1536.4 | 1567.26 | 1453.83 |

The "pm stool median" is the median stool output between the time the subject starts to take the evening dose (17:00 to 18:00 on Day 1) and the time the subject starts to take the morning dose (7 am to 8 am on Day 2). The "am stool median" is the median stool output between the time the subject starts to take the morning dose (7 am to 8 am on Day 2) and midnight on Day 2. The "pm stool mean" and "am stool mean" entries are the corresponding mean values.

It is generally considered that a total stool output of approximately 2500 g is required in order to achieve acceptable bowel cleansing. A stool output of approximately 2500 g or greater than that is thus indicative that a solution has good potential for use as a bowel cleansing solution. Both A2+B3 and A3+B3 resulted in a median stool weight of significantly greater than 2500 g. The commercial MOVIPREP® solution also achieved a median stool output of in excess of 2500 g, as was to be expected. The stool output was highest for A3+B3. Solution B3 was therefore selected to be the morning solution for Part 2 of the study. The observed stool output was achieved for MOVIPREP with the ingestion of 2 litres of investigational solution. For the A2+B3 and A3+B3 solutions, the mean stool weights were achieved using a total investigational solution volume of 1250 ml.

Solutions A2 and A3 were effective in contributing to an effective cleansing with any of the solutions with which they were used. It is seen from the "am stool median" and "pm stool median" figures that the stool output immediately after the ingestion of the A2 and A3 solutions was less copious than after the B solutions. The A2 and A3 solutions contributed to the effective bowel cleansing. Given that the subject will often wish to sleep between taking the first bowel cleansing solution and the second solution, it may be advantageous for the first cleansing solution to result in a slightly lower stool output than the second cleansing solution.

TABLE 8a

Study Part 2: Stool Weight (g); full analysis set (FAS, N = 80)

| Treatment | N | 24 hr Median/g | 24 hr Mean/g | 24 hr STD/g |
|---|---|---|---|---|
| A3 + B1 | 20 | 3128.9 | 2898.2 | 856.6 |
| A3 + B4 | 20 | 2546 | 2453.3 | 775.1 |
| A3 + B5 | 20 | 2440.1 | 2501.2 | 1000.3 |
| A3 + B6 | 20 | 2466.8 | 2485.6 | 496.1 |

TABLE 8b

Study Part 2: Stool Weight (g); full analysis set (FAS, N = 80)

| Treatment | N | pm stool median/g | am stool median/g | pm stool mean/g | am stool mean/g |
|---|---|---|---|---|---|
| A3 + B1 | 20 | 1170.0 | 2146.4 | 1087.59 | 1846.41 |
| A3 + B4 | 20 | 1156.5 | 1467.2 | 1114.64 | 1370.69 |
| A3 + B5 | 20 | 1091.1 | 1448.6 | 1039.42 | 1574.65 |
| A3 + B6 | 20 | 1210.7 | 1436.2 | 1163.93 | 1402.64 |

A3+B1 and A3+B4 resulted in a 24 hour median stool output weight of greater than 2500 g. For the combination A3+B5, the median stool output was just under 2500 g, but the mean stool output was over 2500 g. Thus, all of the solution combinations of the invention (A3+B1, A3+B4 and A3+B5) resulted in a 24 hour mean or median stool output weight of greater than 2500 g.

Considering the data from tables 7a, 7b, 8a and 8b together, B1, B3, B4 and B5 solutions have been shown to be effective bowel cleansing solutions when used in combination with any other solution with which they were used. The particularly copious stool output seen in the "am stool mean" figures shows that the solutions are especially effective.

In the case of A3+B1, the median stool weight was significantly greater than 2500 g. It is again noteworthy that the mean stool weights were achieved using a total investigational solution volume of only 1250 ml.

Solution A3 in combination with reference solution B6 resulted in stool output that was not statistically significantly different from 2500 g.

We claim:

1. A composition for admixture with 300 ml to 800 ml water, wherein the composition is optionally presented in two or more parts, and comprises:
   a) 50 to 60 g of an ascorbate component, the ascorbate component being ascorbic acid, one or more salts of ascorbic acid, or a mixture of ascorbic acid and one or more salts of ascorbic acid;
   b) 10 to 50 g polyethylene glycol; and
   c) sodium chloride and potassium chloride;
wherein the ascorbate component and polyethylene glycol are in a weight ratio of 1.0 to 4.0:1 ascorbate to polyethylene glycol.

2. The composition as claimed in claim 1 comprising:
   a) 50 to 60 g of ascorbate component;
   b) 10 to 50 g PEG having an average molecular weight of 3000 to 4000 Da;
   c) sodium chloride and potassium chloride;
   d) optionally one or more flavouring agents; and
   e) optionally one or more sweeteners.

3. The composition as claimed in claim 1 comprising 1.5 to 3.5 g of sodium chloride.

4. The composition as claimed in claim 1 comprising 1.0 to 2.5 g of potassium chloride.

5. The composition as claimed in claim 1 comprising 40 g of PEG.

6. The composition of claim 1, wherein the solution has a volume of 400 ml to 700 ml.

7. A composition comprising the following components in the following weight ratios:
   a) ascorbate anion provided by ascorbic acid, one or more salts of ascorbic acid, or a mixture thereof: 1.0 to 4.0 parts;
   b) polyethylene glycol: 1.0 part;
   c1) sodium chloride: 0.05 to 0.3 parts; and
   c2) potassium chloride: 0.02 to 0.08 parts.

8. The composition as claimed in claim 7 comprising the following components in the following weight ratios:
   a) ascorbate anion: 1.0 to 4.0 parts;
   b) polyethylene glycol: 1.0 part;
   c1) sodium chloride: 0.06 to 0.2 parts; and
   c2) potassium chloride: 0.03 to 0.07 parts.

9. The composition as claimed in claim 7 which is a dry powder composition.

10. The composition as claimed in claim 7 which is substantially free from any bicarbonate.

11. The composition as claimed in claim 7 comprising the following components in the following weight ratios:
   a) ascorbate anion: 1.0 to 4.0 parts;
   b) PEG having an average molecular weight of 3000 to 4000 Da: 1.0 part;
   c1) sodium chloride: 0.05 to 0.3 parts;
   c2) potassium chloride: 0.02 to 0.08 parts;
   d) optionally one or more flavouring agents; and
   e) optionally one or more sweeteners.

12. The composition as claimed in claim 7, wherein the composition comprises:
   a) 50 to 60 g ascorbate component, the ascorbate component being ascorbic acid, one or more salts of ascorbic acid, or a mixture of ascorbic acid and one or more salts of ascorbic acid
   b) 10 to 50 g polyethylene glycol; and
   c) sodium chloride and potassium chloride.

13. The composition as claimed in claim 7 comprising:
   a) 50 to 60 g ascorbate component, the ascorbate component being ascorbic acid, one or more salts of ascorbic acid, or a mixture of ascorbic acid and one or more salts of ascorbic acid;
   b) 10 to 50 g PEG having an average molecular weight of 3000 to 4000 Da;
   c) sodium chloride and potassium chloride;
   d) optionally one or more flavouring agents;
   e) optionally one or more sweeteners.

14. A kit comprising:
   A) a first sachet comprising a first composition for the preparation of a first colon cleansing solution;
   B1) a second sachet; and
   B2) a third sachet,
wherein the second and third sachets together provide the composition as claimed in claim 1 for the preparation of a second colon cleansing solution.

15. A kit comprising:
   A) a first component being a composition for the preparation of a first colon cleansing solution, the first component comprising:
      (i) 52.5 to 187.5 g PEG having an average molecular weight of 2500 to 4500 Da;

(ii) 1.5 to 15 g of one or more alkali metal sulphates, alkaline earth metal sulphates or a mixture thereof;
(iii) optionally one or more electrolytes;
(iv) optionally one or more flavouring agents;
(v) optionally one or more sweeteners, and
B) a second component being a composition optionally presented in two or more parts for the preparation of a second colon cleansing solution having a volume of 300 ml to 800 ml, the second component comprising:
a) 50 to 60 g of an ascorbate component, the ascorbate component being ascorbic acid, one or more salts of ascorbic acid, or a mixture of ascorbic acid and one or more salts of ascorbic acid;
b) 10 to 50 g polyethylene glycol; and
c) sodium chloride and potassium chloride
wherein the ascorbate component and the polyethylene glycol are in a weight ratio of 1.0 to 4.0:1 ascorbate to polyethylene glycol in the second composition.

16. The kit as claimed in claim 15 wherein:
A) a first sachet comprises:
(i) 52.5 to 187.5 g PEG having an average molecular weight of 2500 to 4500 Da;
(ii) 1.5 to 15 g of one or more alkali metal sulphates, alkaline earth metal sulphates or a mixture thereof;
(iii) optionally one or more electrolytes;
(iv) optionally one or more flavouring agents;
(v) optionally one or more sweeteners,
B1) a second sachet comprises:
(i) 10 to 50 g PEG having an average molecular weight of 2500 to 4500 Da;
(ii) sodium chloride and potassium chloride and/or one or more salts of ascorbic acid; and
B2) a third sachet comprises ascorbic acid,
wherein the optional one or more salts of ascorbic acid in the second sachet (B1) and the ascorbic acid in the third sachet (B2) together providing 50 to 60 g ascorbate component.

* * * * *